US007389245B1

(12) United States Patent
Ashford et al.

(10) Patent No.: US 7,389,245 B1
(45) Date of Patent: Jun. 17, 2008

(54) METHOD AND APPARATUS FOR PROVIDING INCENTIVES TO PHYSICIANS

(75) Inventors: Clint Ashford, Athens, GA (US); Jay Sultan, B gart, GA (US)

(73) Assignee: Clinton B. Ashford, Athens, GA (US)

(*) Notice: Subject to any disclaimer, the term of this patent is extended or adjusted under 35 U.S.C. 154(b) by 366 days.

(21) Appl. No.: 09/648,582

(22) Filed: Aug. 25, 2000

(51) Int. Cl.
*G06Q 10/00* (2006.01)

(52) U.S. Cl. .................. 705/2; 705/4; 705/14

(58) Field of Classification Search ............. 705/2, 705/3, 4, 1, 14, 7, 9, 38, 26, 37; 283/117, 283/54, 56; 702/181; 600/300, 529, 545; 364/401; 707/1

See application file for complete search history.

(56) References Cited

U.S. PATENT DOCUMENTS

| | | | | |
|---|---|---|---|---|
| 5,324,077 A | * | 6/1994 | Kessler et al. .............. | 283/54 |
| 5,557,514 A | * | 9/1996 | Seare et al. ................ | 705/2 |
| 5,819,228 A | * | 10/1998 | Spiro ........................ | 705/2 |
| 5,835,897 A | * | 11/1998 | Dang ........................ | 705/2 |
| 5,845,254 A | * | 12/1998 | Lockwood et al. ......... | 705/2 |
| 5,890,129 A | * | 3/1999 | Spurgeon .................. | 705/4 |
| 5,970,463 A | * | 10/1999 | Cave et al. ................ | 705/3 |
| 6,022,315 A | * | 2/2000 | Iliff ........................... | 600/300 |
| 6,208,973 B1 | * | 3/2001 | Boyer et al. ............... | 705/2 |
| 6,208,974 B1 | * | 3/2001 | Campbell et al. .......... | 705/3 |
| 6,317,700 B1 | * | 11/2001 | Bagne ....................... | 702/181 |
| 6,826,536 B1 | * | 11/2004 | Forman ..................... | 705/4 |
| 2002/0022972 A1 | * | 2/2002 | Costello .................... | 705/2 |

OTHER PUBLICATIONS

Bitran, et al, Provider Incentives and Productive Efficiency in Government Health Services document, Sep. 1992. [Retrieved on Jan. 2, 2004]. Retrieved from Internet. URL: <http://www.phrplus.org/Pubs/hfsmar1.pdf>.*

Patterson, J.A. Jr. Physician Compensation, Incentive Plans, and Tax Issues. Texas Health Law Conference 1997. [Retrieved on Jan. 2, 2004]. Retrieved from Internet. URL: <http://www.texhealthlaw.org/Public/cle/patterson97.pdf>.*

Friedman, H.Website Links May Create Tax for Exempt Orgs; Return Disclosure Rules for Private Foundations; Gainsharing Arrangements. 1999. Greenberg Traurig website. [Ret Jan. 2, 2004]. Retr Internet.URL: <http://www.gtlaw.com/pub/alerts/1999/friedman99f.htm>.*

(Continued)

*Primary Examiner*—C. Luke Gilligan
*Assistant Examiner*—Natalie A. Pass
(74) *Attorney, Agent, or Firm*—Courtney Staniford & Gregory LLP

(57) ABSTRACT

The present invention provides a method of providing a monetary incentive to a health care provider, typically a physician, responsible for treatment decisions of a patient with a condition during an episode of care. Once the patient identity and condition are obtained, a baseline value related to treatment of the condition can be associated. Thereafter, all the claims processed during the episode of care of the patient for the condition can be summed to obtain a total treatment cost. And, if the total treatment is less than the baseline value, then a monetary incentive can be provided to the provider based upon that episode of care.

15 Claims, 25 Drawing Sheets

OTHER PUBLICATIONS

Marsh.Sacrificing Patients For Profits:PhysicianIncentivesTo LimitCare&ERISAFiduciaryDuty.Wash.Univ.LawQutly. V77,No. 4.1999.[Retr.Jan. 2, 2004]. Retr Internet.URL:<http://law.wustl. edu/WULQ/77-4/index.html> and <http://law.wustl.edu/WULQ/77-4/774-1323.pdf>.*

Friedman, H. Appeals Court Rejects IRS Inurement Argument; IRS Approves 'Gainsharing' Programs. Mar. 1999. Greenberg Traurig Alert. [Retrieved Mar. 30, 2005]. Retrieved from Internet. URL: <http://www.gtlaw.com/pub/alerts/1999/friedman99a.pdf>.*

Washlick, J. Physician-Hospital Gainsharing Arrangements. Oct. 1999. Physician's News Digest. [Retrieved Mar. 29, 2005]. Retrieved from Internet. URL: <http://www.physiciansnews.com/law/1099.html>.*

"Celadon Health Signs With Symmetry; Physician Incentive System Will Use Episode Treatment Groups (TM)," PR Newswire. New York: Jun. 20, 2000. p. 1. [Retrieved from Internet Sep. 12, 2006]. URL: <http://proquest.umi.com/pqdweb?did=55354639&sid=10&Fmt=3&clientld=19649&RQT=309&VName=PQD>.*

Boyden A. et al., "The appropriate use of financial incentives to encourage preventive care in general practice," May 2000. [Retreived from Internet Jun. 7, 2007]. URL: <http://www.buseco.monash.edu.au/centres/che/pubs/rr18.pdf>.*

* cited by examiner

| Name | Size | Sample | Description |
|---|---|---|---|
| Family ID | 30 | 368743816 | With Member ID, forms a unique identifier for each patient in the plan |
| Member ID | 2 | 01 | With Family ID, forms a unique identifier for each patient in the plan |
| Patient Sex | 1 | M | Code to indicate gender |
| Patient Age | 3 | 34 | Age of patient |
| Amount Paid | 11 | 897.34 | Adjudicated amount, the amount the payor pays to the provider, which excludes copays and deductibles |
| CPT4 Code | 5 | 21454 | A industry standard code which designates the type pf procedure or action provided |
| First DX Code | 6 | 830 | An industry standard (ICD-9) code which designates the primary diagnosis |
| Second DX Code | 6 | 8481 | An industry standard (ICD-9) code which designates an additional diagnosis, if it exists |
| Third DX Code | 6 | | An industry standard (ICD-9) code which designates an additional diagnosis, if it exists |
| Fourth DX Code | 6 | | An industry standard (ICD-9) code which designates an additional diagnosis, if it exists |
| First Date Of Service | 8 | 6/26/1999 | The date the service was provided (or the first date of a date range) |
| Last Date Of Service | 8 | | The last date of a date range when service was provided, or null |
| Type Of Service | 10 | A | A code which indicates the type of charge, if the CPT4 code is not available |
| Provider ID | 20 | 18772554 | A unique identifier for a provider |
| NDC Code | 11 | 45044964 | An industry standard code which identifies the drug used |

Figure 3A

| Nam | Size | Added by Gr uper Sampl | Descripti n |
|---|---|---|---|
| ETG Assignment | 4 | 723 | A code indicating the ETG Category assigned to this claim, which classifies the episode type |
| Episode Number | 10 | 98614 | A sequential counter used to identify distinct episode instances |
| Episode Cluster | 3 | 3 | A subset of an episode instance |
| Episode Type Flag | 1 | 1 | A code indicating the confidence in the accuracy of the episode instance |
| Record Type Flag | 1 | M | A code indicating the category of the expense |
| Cluster Provider ID | 20 | 18772554 | The provider who is responsible for the claim which is the basic claim for this cluster. |

FIG. 3B1

*Added by Incentive Administrator*

| Nam | Siz | Sample | Description | Entity |
|---|---|---|---|---|
| EPG Assignment | 5 | 1982 | A code indicating the EPG Category assigned to this claim, which classifies the episode type | Episode Instance |
| EPG Number | 15 | 928776 | A sequential counter used to identify distinct episode instances | Claim |
| Outlier | 1 | 0 | A flag to indicate that the episode is an outlier | Episode Instance |
| Do not Pay Incentive | 1 | 0 | A flag to indicate that the episode should not have an incentive paid | Episode Instance |
| Responsible Physician | 20 | 18772554 | The provider who is responsible for the EPG | Episode Instance |
| Baseline | 11 | 2105 | Default expected cost of the episode, used as a normative measure of cost | Episode Category |
| Adjusted Baseline | 11 | 1015 | The baseline value for the episode instance, adjusted for comorbidities or other reasons | Episode Instance |
| Savings | 11 | 101 | The savings achieved for this episode instance - if negative, indicates that the total cost was greater than the baseline | Episode Instance |
| Referring Physician | 20 | 20715432 | The physician who referred the patient, if any | Episode Instance |
| Default Physician | 20 | 10217824 | The default physician to use for the patient if no Responsible Physician can be determined | Patient |
| Floor Value | 11 | 450 | The minimum cost an episode instance is expected to cost | Episode Category |
| Ceiling Value | 11 | 2200 | The maximum cost an episode is expected to cost | Episode Category |
| Total Actual Cost | 11 | 914 | The total payments made for the claims in the episode | Episode Instance |
| Serial Episode Indicator | 1 | 0 | Indicates possible serial episode gaming validation | Episode Instance |
| Do not Check for Serial Episode Indicator | 1 | 0 | Indicates that this episode instance should not be checked for a serial episode gaming validation | Episode Instance |
| Do not Check for Floor Indicator | 1 | 0 | Indicates that this episode instance should not be checked for a Below Floor validation | Episode Instance |
| Below Floor Indicator | 1 | 0 | Indicates possible below floor gaming validation | Episode Instance |
| Possible Upcode Indicator | 1 | 1 | Indicates possible upcoding gaming validation | Episode Instance |
| Prorata factor | 5 | 0.85 | Percentage of total treatment (and expense) to be allocated to this episode where the patient enters or leaves the plan while an episode is in progress. Most episodes will be 1 | Episode Instance |
| Comorbidity Factor | 5 | 1.25 | Ratio used to adjust a baseline for the presence of a comorbidity condition for the patient | Cormorbidity Instance |

FIG. 3B2

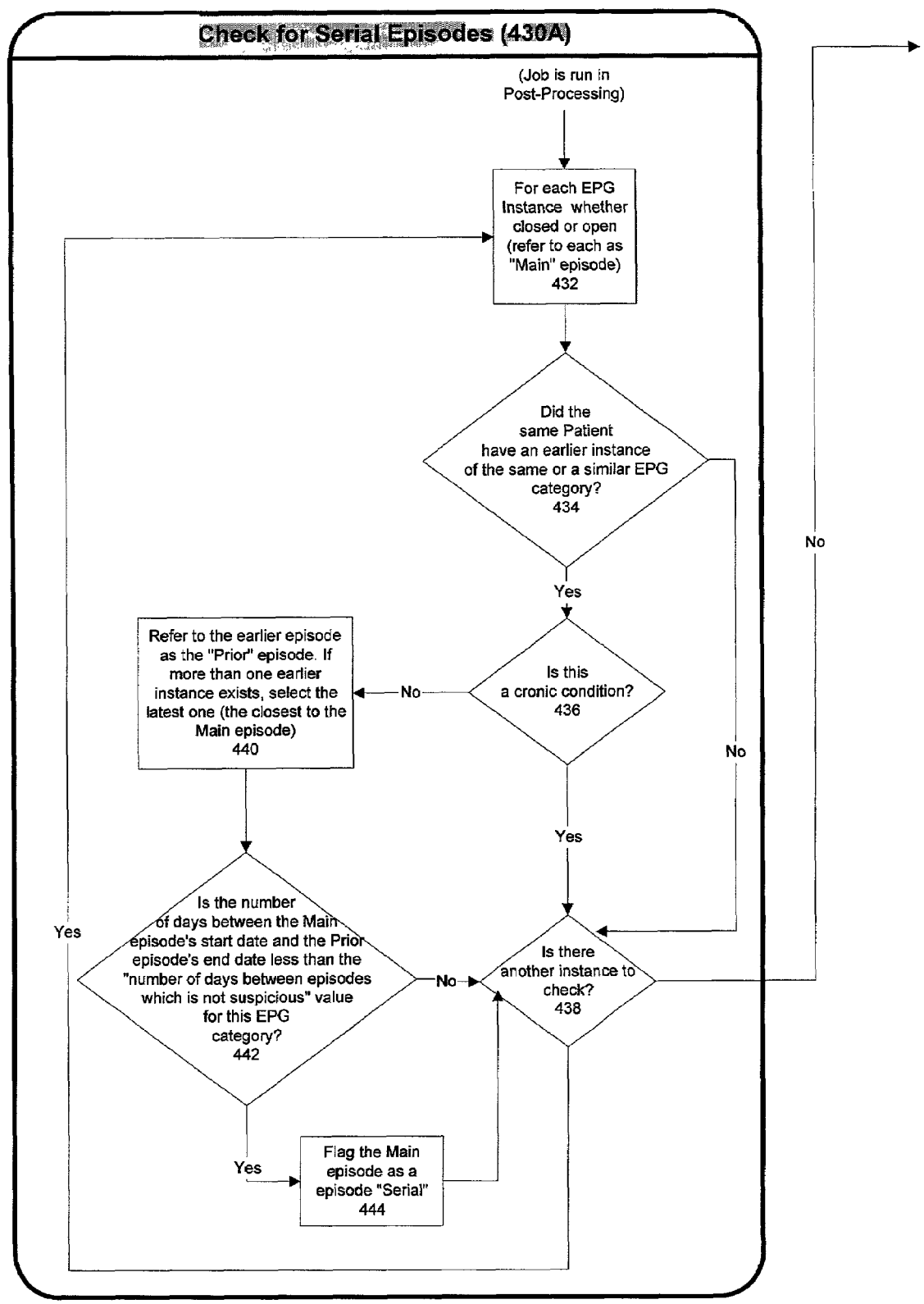
Figure 8A-3 (1 of 4)

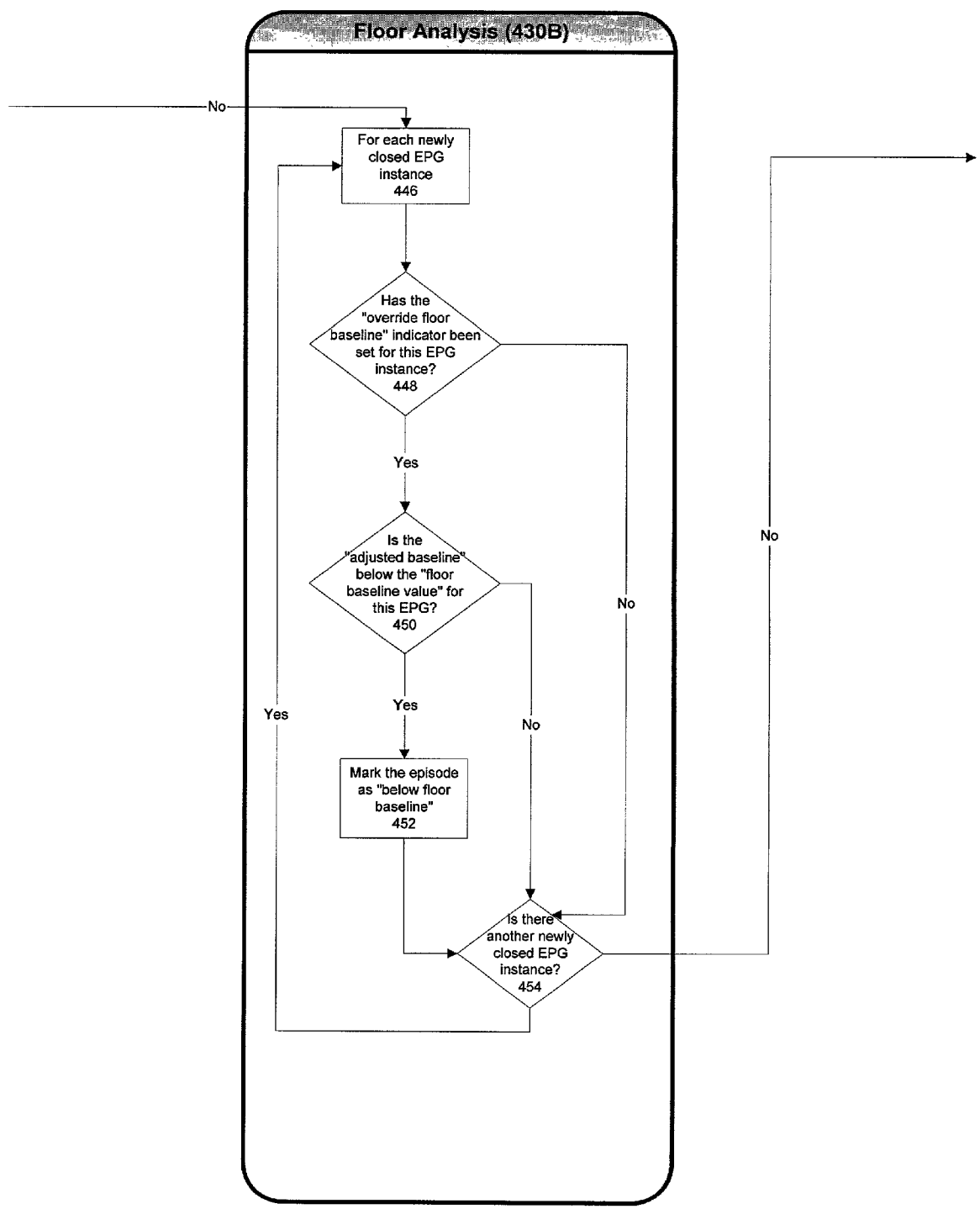
Figure 8A-3 (2 of 4)

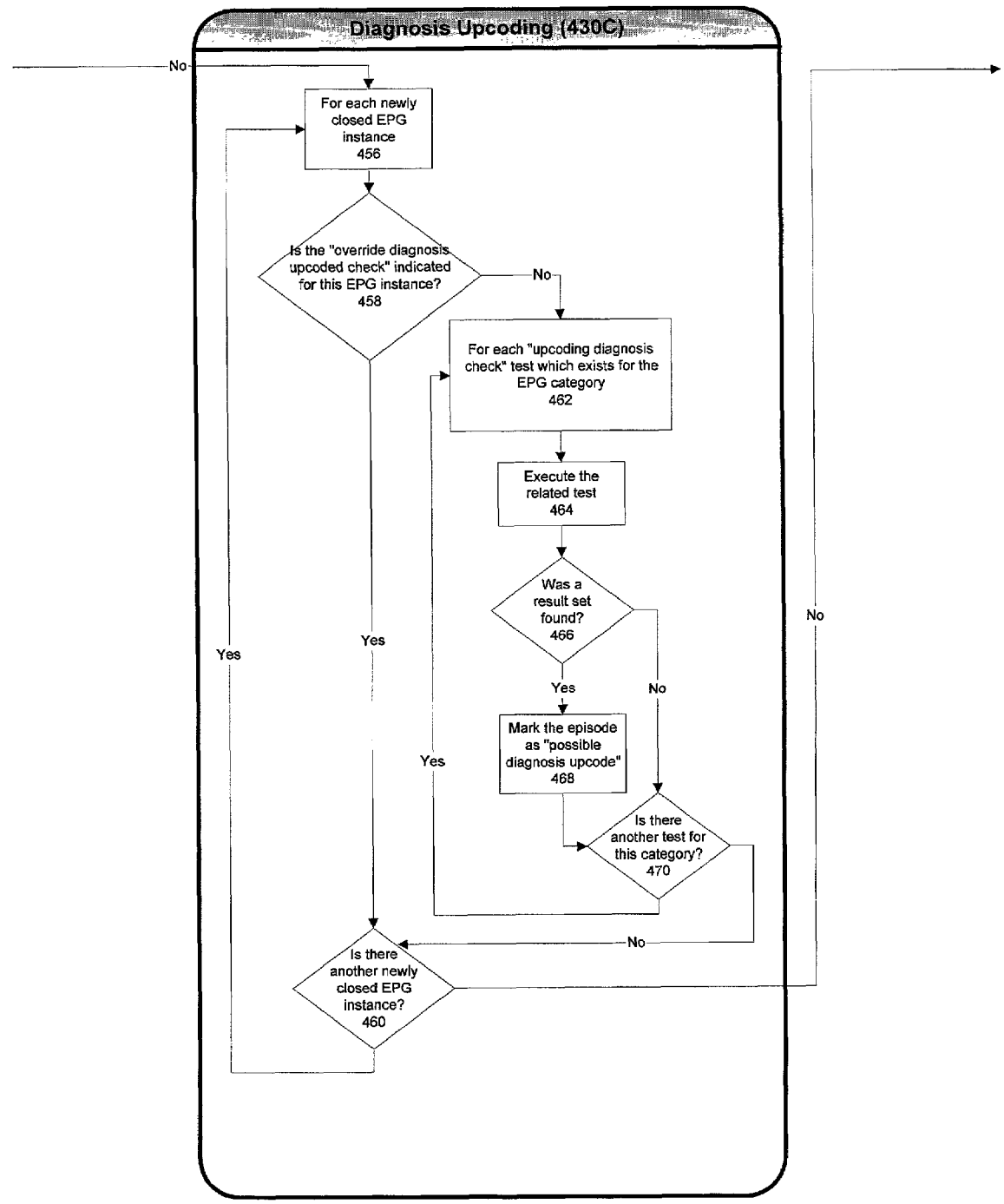
Figure 8A-3 (3 of 4)

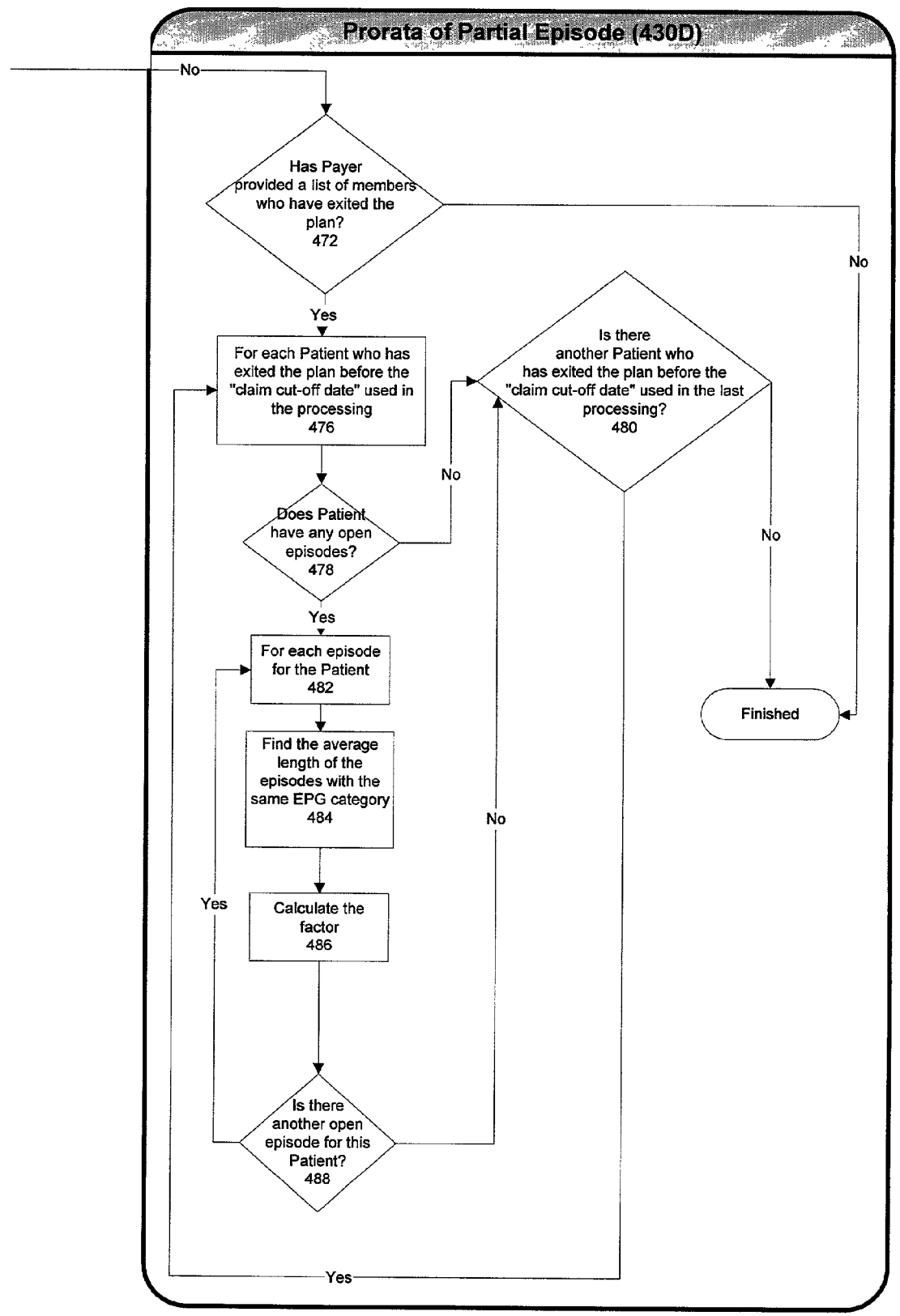
Figure 8A-3 (4 of 4)

METHOD AND APPARATUS FOR PROVIDING INCENTIVES TO PHYSICIANS

FIELD OF THE INVENTION

The present invention relates to a method for providing incentives to physicians, and, more particularly, a system, primarily implemented using a software program, for ascribing a baseline value to instances of care, and rewarding physicians for treating a specific instance of care for an amount less than the baseline value.

DESCRIPTION OF THE RELATED ART

The health care industry provides medical treatment to the population at large. The insurance industry is in the business of sharing risk. Both of these industries are forced to work together when it comes to determining health care premiums for individual patients. Over the years, the health care industry has been able to provide better preventive care, as well as more sophisticated treatment, which all come at a cost and tends to increase health care premiums for individuals.

Kaiser Permanente is an example of merging a health care system and an insurance company into a single entity. Began in the 1940's, a premise of the merger of the health care system with the insurance company was that it would have an increased oversight capability, and thus be able to reduce cost. In order to do this, however, participants in the system were required to use physicians and services provided from within that system, thus reducing the choice that the consumer has to select his or her own physician.

At the other end of the spectrum is a system where the healthcare system and insurance company are entirely separate. The insurance company provides insurance to the customer, and the customer can then freely choose physicians, course of treatment and the like, and a fee for the service is paid by the insurance company to the provider. While such a system allows greater choice, it also results in greater costs.

Between the above two types of systems are health maintenance organizations (HMO's) and managed care organizations (MCO's) that have evolved. By allowing for member patients to choose from among a network of physicians, facilities, clinics and the like that make up the HMO or MCO, savings are incurred, which thereby lower the overall cost, with some of the savings being passed on to the member patients. In such systems, one of the manners of payment is based on "capitation," in which the insurance company is paid a monthly fee by the patient or his employer, and the physician for that patient is paid some small percentage of that monthly fee. If the patient never receives any treatment, then the physician obtains a windfall, but if the patient requires more treatment than that covered by the monthly fee, the physician takes an effective loss. The net result is that there is an incentive for the physician to keep their own costs as low as possible; many times, it has been argued, to the detriment of the health of the patient.

In large part as a result of the capitation, what is known as "utilization review" has evolved, in which a particular formula is established to determine what care to provide in a specific case. Thus, for instance, even if a physician believes that a surgery is needed, utilization review may determine that a specific test with a particular result is needed in order to qualify for that surgery. As a result there is a negative means to keep costs down.

Point of service (POS) plans have also been developed with the intent to allow a greater freedom of choice of physicians and free access to that physician than are available in a capitation system. Typically more expensive than an HMO, a POS plan is intended to allow the patient to choose the physician of choice, and the insurance company agrees to pay some percentage, such as 80% of fees incurred, after some deductible. In practice, these plans typically do not reimburse the full percentage that was "agreed" to, in large measure due to "usual and customary" fees that the insurance company uses to determine the fees for procedures performed, which are typically less than the fees charged by the physician the patient chose. The net effect, therefore, is to incentivize the patient to use in-network physicians, which physicians the insurance company can then exert more control over in terms of their fees and costs, or cause the patient to bear more of the costs directly out of the patient's own pocket.

Over the last few decades, discussion has raged as to which of the above types of plans provide the best balance between patient care and controlling of costs. That debate still rages. But while that debate rages, attempts to contain costs continue to increase and systems have been developed to assist in containing costs. While capitation fees are one form of reimbursement, organizations have also provided incentives to groups of doctors. In one more recent form of incentive, if, based on all of their patients, the total fees and costs that have been incurred by the group are below the projected amount an incentive is paid. While such a system provides an incentive for the group to keep fees and costs low, such a system does not, on an episode of care basis for a particular patient, correlate the total cost of the services provided to a particular incentive. Accordingly, there is no direct correlation between the incentive and the specific care provided to a particular patient. Further, given the systems as described above, with an emphasis on lower costs, abuses unfortunately occur. As a result the health care system has become perceived as providing less than effective treatment to patients, with ever increasing costs that are in more and more instances passed on to the patient.

SUMMARY OF THE INVENTION

It is an object of the present invention to provide a system that incentivizes providers, and specifically responsible physicians, to provide effective care on an episode of care basis for each individual patient.

It is a further object of the present invention to identify a single physician who is responsible for the primary decision on the appropriate treatment path for each episode of care for a patient, and to then incentivize that physician to provide effective care for that episode of care basis for that patient.

It is a further object of the present invention to allow an outside party administrator to implement the incentive plan, thereby maintaining a system of checks and balances between the physicians or other health care providers and the insurance companies.

It is a further object of the invention to provide a substantially automated system that determines a responsible provider and the incentives from data associated with the episode of care for the particular patient.

It is a further object of the present invention to consider comorbidity, outliers, or gaming when determining incentive payments.

The present invention is capable of attaining the above-recited objects, and others, either separately or in combination as defined in the claims below. In general, however, the invention provides a method of providing a monetary incentive to a health care provider, typically a physician, responsible for treatment decisions of a patient with a condition during an episode of care. Once the patient identity and condition are obtained, a baseline value related to treatment of the condition can be associated. Thereafter, all the claims processed during the episode of care of the patient for the condition can be summed to obtain a total treatment cost. And, if the total treatment is less than the baseline value, then a monetary incentive can be provided to the responsible provider based upon that episode of care.

The present invention also is able to provide a method of automatically processing a plurality of claims data for a patient treated for a condition to determine a responsible provider, and in most systems a responsible physician, for an episode of care. Initially, the providers who ordered procedures for the patient are identified. Then, a defining procedure is identified for the condition, if such a defining procedure exists. If the defining procedure exists, then the provider who performed the defining procedure is assigned as the responsible provider. If the defining procedure does not exist, however, that provider who was responsible for incurring a predetermined percentage of costs for the episode of care can be assigned as the responsible provider.

BRIEF DESCRIPTION OF THE DRAWINGS

These and other objects and advantages of the present invention, along with the best mode for practicing it, will become apparent to those skilled in the art after considering the following detailed specification, together with the accompanying drawings wherein:

FIGS. 3A-3B1-2 illustrate samples of claim data and information added by the incentive administrator according to the present invention;

FIG. 6A-1 illustrates an overview flowchart of preprocessing of claims data according to the present invention;

FIG. 6A-2 illustrates a flowchart of game checking of claims data according to the present invention;

FIG. 6A-3 illustrates a flowchart of preprocessing logic adjustments according to the present invention;

FIG. 6A-4 illustrates a flowchart of adjusting previously closed episodes of care according to the present invention;

FIG. 8A-1 illustrates an overview flowchart of post-processing of claims data according to the present invention;

FIG. 8A-2 illustrates a flowchart of episode payment group encoding according to the present invention;

FIG. 8A-3(1-4) illustrates a flowchart of game checking grouped claims data according to the present invention;

FIG. 8A-4 illustrates a flowchart of post-processing logic adjustments according to the present invention;

FIG. 9A-1 illustrates a flowchart of determining a responsible physician according to the present invention;

FIG. 9A-2 illustrates a flowchart of determining a default physician according to the present invention;

DETAILED DESCRIPTION OF THE PREFERRED EMBODIMENT

A detailed description of the preferred embodiment of the present invention will now be described. One aspect of the present invention is the overall method by which a specific physician is rewarded for reducing costs related to a specific episode of care for a specific patient. Another aspect of the present invention is an automated system using claims data to determine both the physician to whom the incentive should inure, as well as the amount of the incentive.

As will be described, in contrast to a conventional system, as described above, where there exists an insurance company, here also referred to as a "payer," and a. "provider," such as a physician, clinic, or hospital, present invention also includes an incentive administrator. The incentive administrator performs the functions described hereinafter and, significantly, because the incentive administrator acts independently of both the payer and the provider, and also shares in the savings achieved, provides the checks and balances between the payer and the provider that does not exist in a conventional association between payers, such as insurance companies, and providers, such as physicians. Accordingly, while the incentive administrator, the payer, and the provider are all interested in providing appropriate health care to patients, the present invention recognizes that it is the providers (in most instances the responsible physician) that require the ability, on an individual patient basis, to independently make decisions on the appropriate treatment, but must also shoulder the responsibility for those decisions.

Accordingly, an aspect of the present invention is to reward those providers who have the greatest ability to substantially influence the overall cost of treatment for an episode of care. By rewarding those providers who have the greatest ability to influence the overall cost of an episode of care for a patient, those providers can recognize a benefit if the most cost-effective ways are used in treating the patient. Since, however, those same providers are subject to scrutiny—i.e., malpractice lawsuits—if they do not perform their services adequately, they already have an incentive to provide that care which is necessary to maintain the health of the patient, not to mention the Hippocratic Oath that physicians must take in any event. Also, the invention preferably uses an essentially open panel, so the physician must market their practice to patients, catering their practice the patients and potential patients in an open market, competing against other physicians. The quality of medical care would be a foremost component of any physician's marketing, thus providing yet another reason to provide high quality care. Further, the invention includes a process to identify physicians who do not provide the care necessary to meet accepted industry norms.

Figure 1:
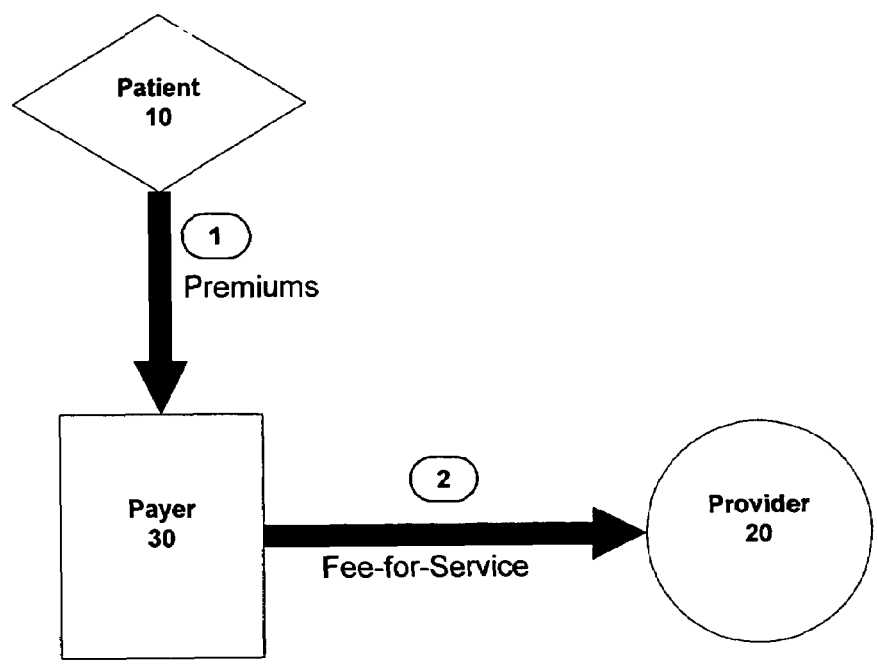
FIG. 1 illustrates the overall method if providing incentives according to the present invention.
Figure 1:
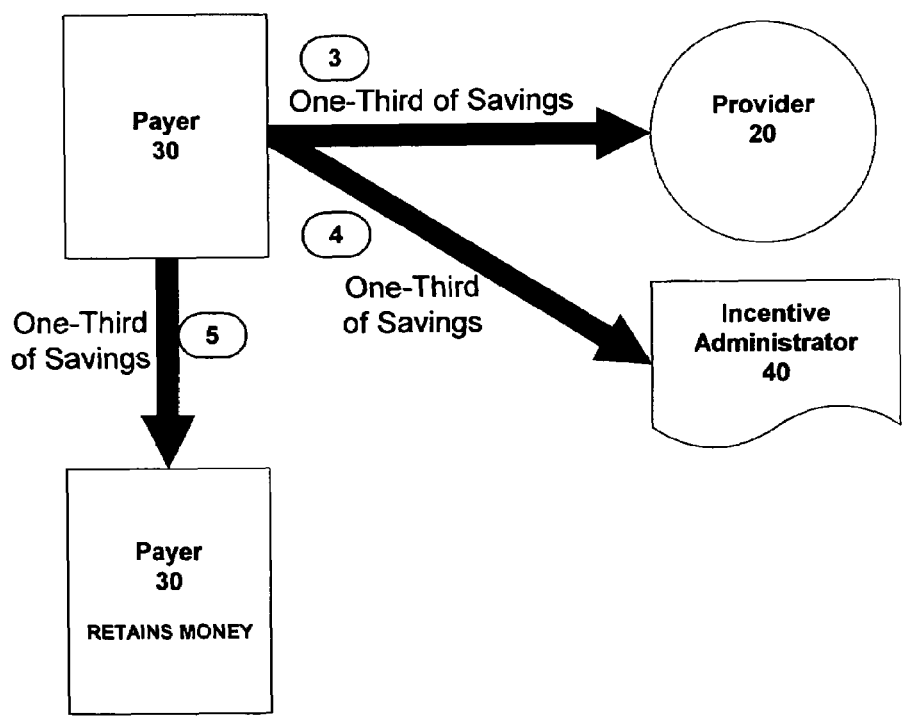

With the above in mind, reference is now made to FIG. 1, which shows the overall flow of funds between the various parties that exist in the health care system according to the present invention. As shown, in step 1, premiums are paid by a patient 10 to a payer 30. This payer 30 can be an insurance company, a self-insured employee, or other organization. As shown in step 2, certain of the fees received by the payer 30 are paid out to different providers 20 for services rendered. The provider 20 can be a physician, hospital or other health care organizations or providers.

The fee for service that is paid in step 2 can be based on the existing structure between the payer 30 and the provider 20, or an alternate structure that recognizes that advantages contained by the present invention. In any event, the present invention, for each different type of episode of care, establishes a baseline value that is used to determine the typical fee that would be paid for treating that type of patient. This baseline value can be varied in manners discussed hereinafter, and will also differ depending upon the geographic location, the cost of living, and other variables, none of which are pertinent to an understanding of the present invention. What is pertinent is that for a single episode of care, which may require repeated visits for the treatment of an illness and all of the tests and procedures associated therewith, or maybe only require a single office visit, there is a baseline value that is associated with each type of episode of care.

The total cost of each episode of care is determined as a result of the choices made by the provider 20 and, in particular, a specific physician or person who has control over the costs associated with that episode of care as described hereinafter. The difference between the total cost for the specific episode of care and the predetermined baseline value for that episode of care equals the resulting savings that have been realized. The resulting savings is then split between a provider 20 (in most instances the responsible physician), the payer 30, and the incentive administrator 40, as illustrated by steps 3, 4, and 5. As also shown in FIG. 1, in a preferred embodiment of the present invention, this savings is split in equal thirds, such that each of the provider 20, payer 30, and incentive administrator 40 retain one-third of the resulting savings. It is understood, however, that these percentages can vary as negotiated between the parties.

With an understanding of the overall objective of the present invention being described, the aspect of the present invention dealing with implementation of the program according to the present invention will now be described. Initially, with reference to FIG. 2, there will be described at a high level the flow of data between the patient 10, the provider 20, the payer 30, and the incentive administrator 40. Thereafter, once this flow of data is understood, a more detailed explanation of the manner in which the incentive administrator 40 uses the data it receives to implement the incentive-based program according to the present will be described.

Figure 2:
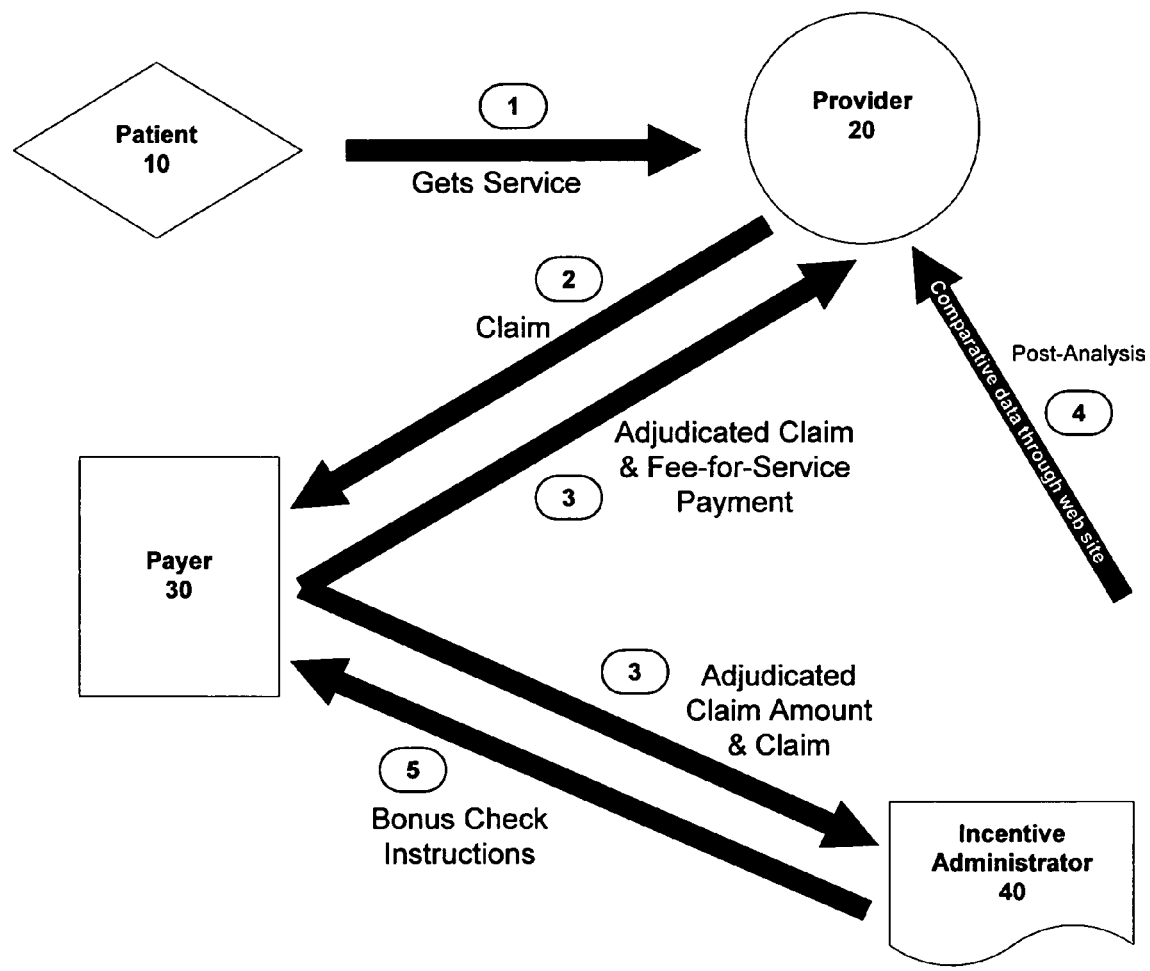
FIG. 2 illustrates an overview of the flow of data between parties according to the present invention.

With reference to FIG. 2, there is shown that the patient 10 in Step 1 receives a service from the provider 20, which can be a physician, hospital, or other health service organization. Based upon the service provided by the provider 20, in Step 2, the provider 20 submits a claim to the payer 30 for that service. Each time the patient receives any service, whether that is a procedure performed by a physician, a test performed by a laboratory, the filling of a prescription, or other related services, a separate claim for each will be provided. Each procedure is identified, typically, by a code such as a CPT4 procedure code. Further, many claims will contain a diagnosis code or codes, such ICD-9 diagnosis code codes, which can be used to assist in determining the condition of the patient automatically, as described further hereinafter. Also, certain claims may contain an NDC drug code, identifying the prescribed medication. The different claims for that patient are then aggregated when determining the total cost for an episode of care. Furthermore, if a single patient is being treated for more than one type of condition, this may equate to more than 1 episode of care, and thereby require that each submitted claim identify the specific episode of care for which the patient is being treated.

The payer 30, upon receipt of the claim information, uses that information to determine an adjudicated claim amount. Using this adjudicated claim amount, the payer 30, as shown in step 3, can make a fee-for-service payment back to the provider 20, provide written documentation relating to the adjudicated claim, and will also provide this same adjudicated claim information and the original claim to the incentive administrator 40. An example of the claims data that is submitted by the payer 30 to the incentive administrator 40 is illustrated in FIG. 3A.

The incentive administrator determines, based upon the claim data for each completed episode of care, whether any incentives should be paid according to the present invention's scheme, as described above. Incentive administrator 40 will preferably add certain additional information to the claims data, as will be described in further detail hereinafter, in order to determine if an incentive payment should be made and its amount. The information that is added to each claim and to the aggregation of claims in an episode instance, however, is illustrated in FIG. 3B. Once that determination is made, the incentive administrator 40 will provide to the provider 20, as shown in step 4, post-analysis comparative data that allows the provider 20 to determine whether, for various instances of different episodes of care, how the provider 20 ranked as measured against baseline values. The post analysis comparative data can also contain suggestions on how that provider 20 could change the manner in which services are provided so that quality care can be achieved in a more cost-effective manner, thereby allowing that provider 20 to alter his practice in subsequent situations, and thereby realize a greater incentive in such situations. Also, as shown in step 5, the incentive administrator 40 sends bonus checks instructions to the payer 30 so that, if there has been a savings for that episode of care, as will be described further hereinafter, the payer 30 can use that information to determine the incentive payment to the provider 20 and the incentive administrator 40.

So that the above is more clearly understood, prior to describing the system used to implement the present invention, a specific example will be provided that describes how this system will work.

EXAMPLE

In 1999, in a medium-sized town, there is a dominant insurance company, payer 30, and 20 obstetricians who deliver 1,000 babies per year under the insurance company's health plans. Each obstetrician delivers an average of 50 babies per year. The average fee for childbirth (all C-sections and conventional deliveries combined) has been $2,500 for the OB/Gyn fee, plus $7,500 for hospital care, laboratory, surgical assistant fees, consultations anesthesia fees for epidurals as well as general anesthesia, pathology fees, normal newborn care, etc. Hence, an average of $10,000 per baby, or $10,000×1,000 babies=$10 million per year which is paid by the insurer for all obstetrical care. The twenty OB/gyns are grossing $2,500,000 (or averaging $125,000 each) for obstetrical fees for patients covered by this particular insurer.

Incentive administrator 40 works with the physician coordinator to cut costs beginning on Jan. 1, 2000. There is a negotiated cut in fees by 20% off current rates for both physicians and hospitals. If utilization remains constant, it will now cost the insurance company a total of $8 million, or a total of $2 million less than they are currently paying for obstetrical care. Furthermore, utilization is reduced by having the team leader actively working to cut utilization rates by the following: (1) reduce C-section rates; (2) shorten time spent in the hospital both before and after delivery; (3) reduce unnecessary laboratory, pharmacy and sonogram utilization; (4) reduce usage of epidurals for labor (this will result in shorter labors, fewer C-sections and no anesthesiologist fee); (5) home health care is used for treatment of dehydration, pre-term labor and other antenatal problems; (6) better pre-natal care and wellness measures during the pregnancy. The list can go on and on. Overall, costs are reduced by another $1 million. Total savings are, for example, 30%, or $3 million, off of the payer 30's annual obstetrical bill.

The payer 30 retains one-third of the overall $3 million savings, or $1,000,000, as "extra profit," the incentive administrator 40 is paid one-third, or $1,000,000, to cover over head and profit, and the remaining one-third, or $1,000,000, is divided among the physicians. Amongst those physicians, it has been decided that a fraction of the savings would be paid to the physician coordinator and the remainder would be split among the participating obstetricians on the basis of cost savings achieved for each patient by the responsible physician. The average rebate would be $40,000, but it would be distributed on the basis of actual cost savings below a certain baseline. In this example, a baseline of $8,000 per delivery is used since this is the amount the insurance company would spend if there were not savings beyond the preferred provider discounts, and only 5 physicians A-E of the 20 physicians are discussed.

An average physician, Dr. A, delivered 50 babies with an average cost to the insurer of $7,400, a savings of $600 below the baseline. Dr. B delivered 60 babies with an average cost of $8,000, even with the baseline. Dr. C delivered 40 babies with an average cost of $8,200, $200 over the baseline. Dr. D delivered 50 babies at an average cost of $7,000, $1,000 below the baseline and Dr. E delivered 60 babies with an average cost of $6,500, $1,500 below the baseline. The product of the savings per delivery and number of deliveries can be used to determine savings for the period that each physician will get.

|       | Babies | Savings (below baseline) | Total Savings |
|-------|--------|--------------------------|---------------|
| Dr. A | 50     | 600                      | 30,000        |
| Dr. B | 60     | 0                        | 0             |
| Dr. C | 40     | (200)                    | 0             |
| Dr. D | 50     | 1,000                    | 50,000        |
| Dr. E | 60     | 1,500                    | 90,000        |

Observations relating to these incentives are helpful to an understanding of the present invention:

Doctor A. She is an average saver. Her rebate of $960 per patient more than makes up for the 20% she discounted off her fees to become a preferred provider. She, herself, is earning as much as ever but is also becoming a more efficient provider as far as overall costs are concerned.

Doctor B. No rebate will go to him. The team leader could work closely with him in the future to improve his cost effectiveness.

Doctor C. No rebate goes to him either. His practice has lower than normal volume and he is actually incurring more costs for the insurer. Should he not change his practice patterns, the team leader could have the power (and would have the incentive) to have him removed as a preferred provider.

Doctor D. Though his practice volume is average (50 patients), he is saving more than $1,000 in decreased utilization per delivery. He is, in turn, recouping far more than 20% discount he gave up to become a preferred provider.

Doctor E. He delivered a high volume, 60 babies last year. Nevertheless, he is by far the most cost-efficient provider among doctors A-E. He probably: has a very low C-section rate because of conscientious management of labor and delivery; anticipates problems and treats them effectively early on; handles after-hours calls quickly by telephone or sees patients in his office, rather than sending them to the emergency room. To reward this physician for his extra skill, hard work and efficiency, he will receive a rebate of $144,000, or $2,400, for each baby he has delivered. He will actually be earning an average of $4,400 per delivery, or 76% more than the current fee of $2,500!

Dr. E is being rewarded more because he is working smarter and harder than anyone else. Traditional fee-for-service compensation by CPT code rewards all doctors similarly. However, under this system of the present invention, the more skilled and cost-effective practitioners are rewarded more than sloppy or inefficient practitioners.

Under the system, the physician coordinator can help all of the doctors analyze Doctor E's methods and apply them to their own practices. They may respond to incentives by emulating much of what Doctor E does and may also add innovations of their own. The following year, several other doctors may be practicing as efficiently (or perhaps even more efficiently) than Doctor E.

With the overall business method of the present invention having been discussed, other aspects of the present invention will now be described. Aspects include those relating to the manner in which the incentive administrator receives and processes data from the payer 30 and then provides results back to the provider 20 regarding whether incentives are due, how much they should be. Information is also provided back to the provider 20 in the form of better practices information, as has been described previously.

As has also been mentioned previously, an advantage of the present invention is that data that is electronically received can be automatically processed in most instances although, as noted hereinafter, in certain instances manual review is necessary. Those instances will be described hereinafter as well.

Figure 4:
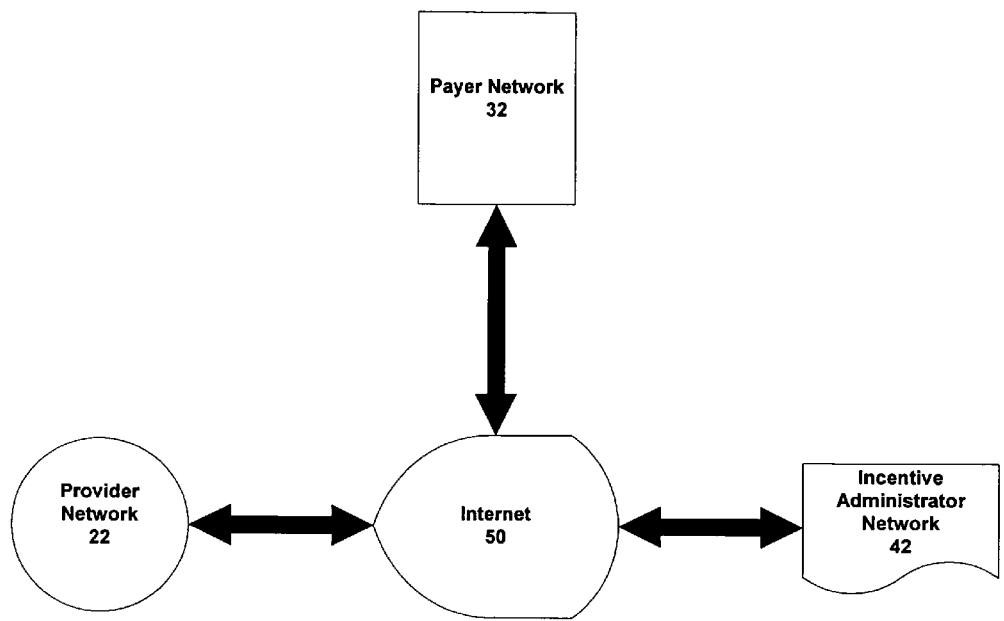
FIG. 4 illustrates an example of the computer networks of various parties according to the present invention.

As illustrated in FIG. 4, very generally, there is shown a provider network 22, payer network 32, and an incentive administrator network 42, each of which can communicate with others through the internet 50 or some other type of computer network. Each of the networks can contain, for example, a UNIX server on which a database is located, a UNIX web server that allows for connection via the internet to various users, as well as a Windows-based computer that allows for certain specific application programs to be run which are part of the present invention. It is understood, however, that the applications described hereinafter can be written so that the various operations can take place on a variety of computers. It is, therefore, unimportant what type of computer is being used.

Figure 5:
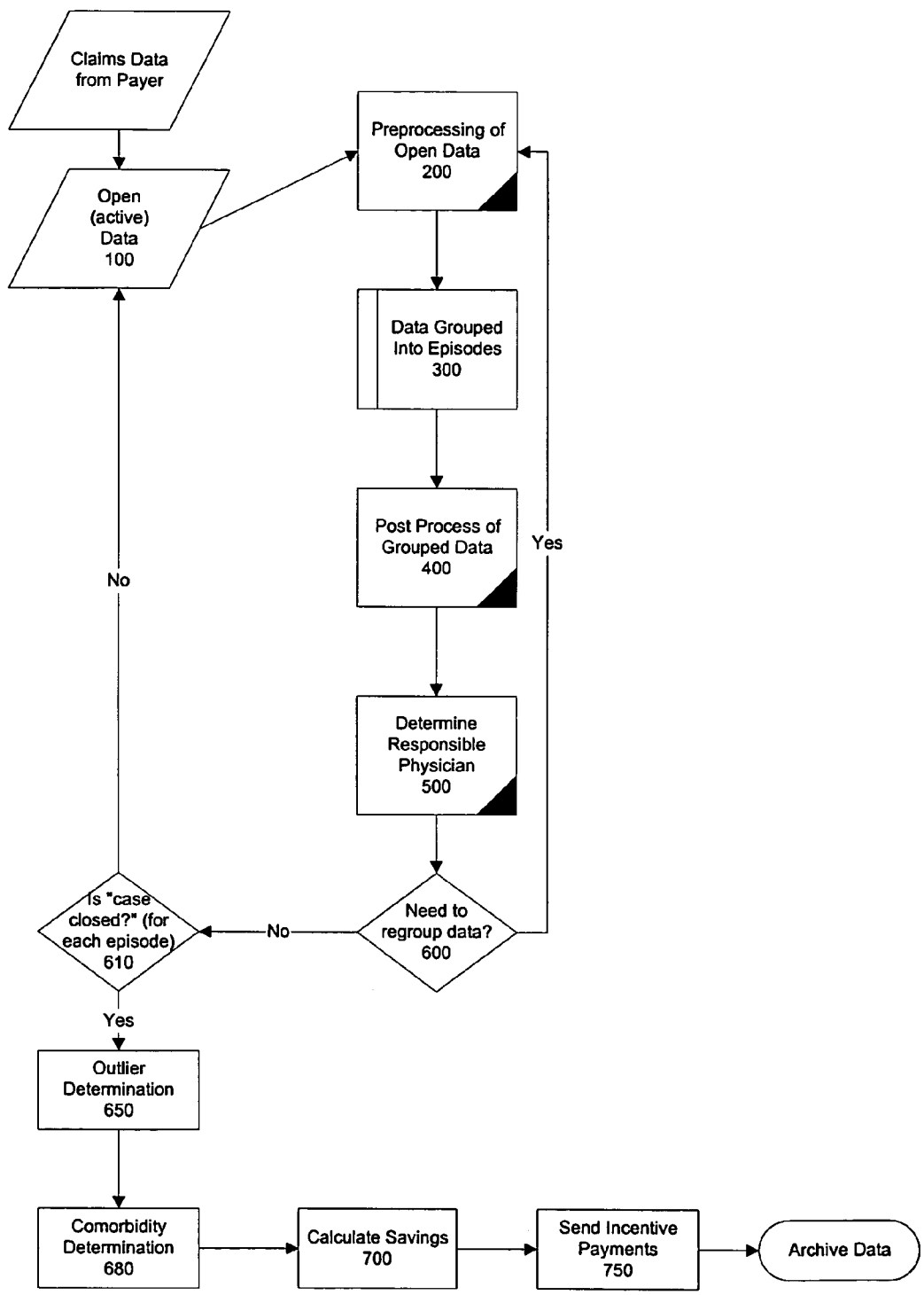
FIG. 5 illustrates an overview flowchart of the incentive program according to the present invention.

FIG. 5 illustrates an overview of the processing of claims data by the incentive administrator 40. This claims data is received weekly, monthly, or at some interval so that the claims data from the payer 30 can be added to the previously received open or active data. As shown in FIG. 5, step 100 illustrates the inclusion of the new claims data to the previously received, and still existing, open data. By "open data" it is meant specific claims for different patients for which the episode of care is still open. In this regard, there are conventionally known various methods for determining whether an episode of care is still open. One method of determining whether an episode of care is open or closed is to set a predetermined window in terms of the number of days from the initial visit by the patient 10 with the service provider 20. The initial visit for an episode of care can be determined from the claims data, and the period of time or window for closing that episode of care can be determined based upon the earliest claim for that type of episode of care. Thus, as shown in step 100, the new claims data is added to the previously received and still open active data. Thereafter, in step 200, this open data will be pre-processed, to take into consideration a number of factors as described further hereinafter. Once this open data is preprocessed in step 200, step 300 follows in which the data is grouped into specific episodes of care. Thus, all of the various claims for a particular episode of care associated with a particular patient can be grouped together. The grouper uses the procedure codes, the diagnosis codes, the drug codes, and other information in the claims associated with each patient to identify those claims that relate to a particular episode of care.

Once this data is grouped into particular episodes of care in step 300 as described above, post-processing of the group data takes place in step 400. This post-processing will be described further hereinafter. Also, a step 500, which is shown as being subsequent to the post-processing within step 400 but, in fact, can occur during a portion of the post-processing of group data as described hereinafter, will occur. In step 500, a determination is made of the physician that is responsible for the particular episode of care for the particular patient. This step is significant since it is used in determining the particular physician, or other provider 20, that is to receive an incentive, if one is to be given. Thereafter, in step 600 there is a decision step performed that determines whether errors exist in the data. After having had an initial preprocessing, grouping, and post-processing, there may be errors contained in the grouped data. For example, the step 400 post-processing logic adjustments can cause the claims data to be altered, and the thus altered claims data will typically need to be regrouped. Thus, when the post-processing logic adjustments are made, a regroup field can be set to indicate that regrouping in step 600 is needed. This process repeats until there are no problems that remain to be edited.

Thereafter, step 610 follows in which it is determined whether any of the episodes that have been grouped together are now closed. If not, then the data associated with non-closed episodes is returned to the open data set described in step 100 and will be used at the next periodic processing of the data.

For each closed episode, however, there then needs to be determined whether an incentive payment should be made. Initially, however, an outliers test step 650 is performed, described further hereinafter, to remove episodes of care that are extremes. Once those are removed, in step 680 there is a step that adjusts for comorbidity, otherwise known as effects of one illness that can exacerbate or make easier the treatment of another illness. Once comorbidity is determined, then in step 700 there is a step of calculating the incentive payments, followed thereafter, by step 750 of making payments to various providers, the payer, and the incentive administrator.

Figures 1, 6A:
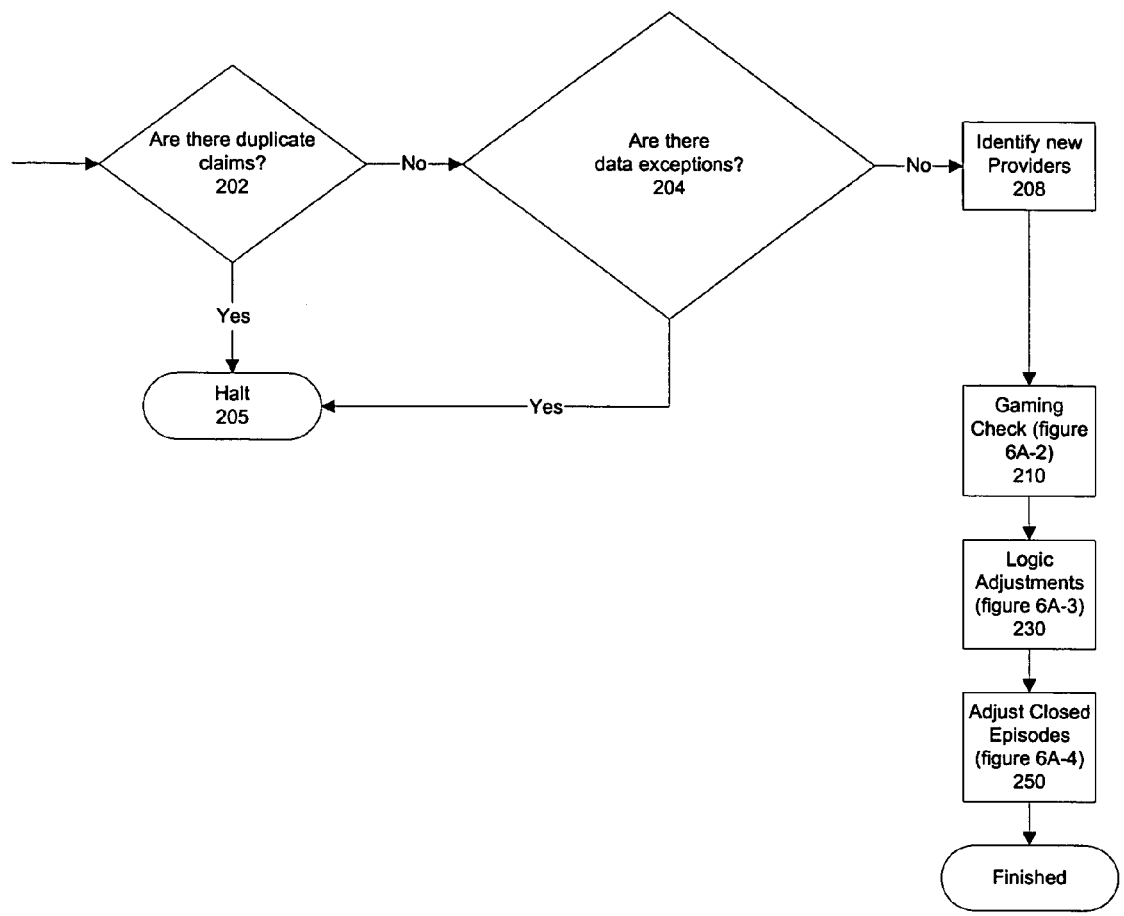
Figures 2, 6A:
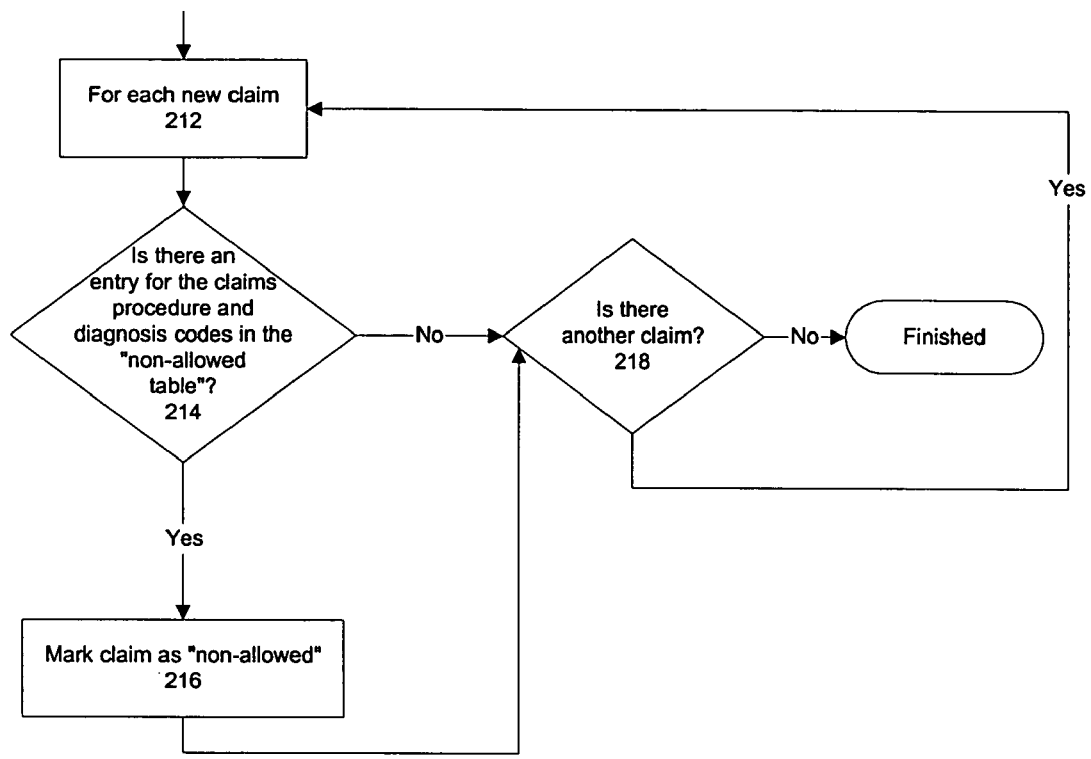

Having described, in FIG. 5, an overview of the processing that takes places automatically by the present invention, the details of this processing will now be described. With reference to FIG. 6A-1, details of the preprocessing of claims data will now be described. Initially, as illustrated in FIG. 6A-1, in step 202, all of the open claims are compared against each other to determine whether there are duplicate claims. If there are any duplicate claims, those duplicate claims are removed, as illustrated in halt step 205. For those claims that are not duplicates, they are then operated upon step 204, to determine whether there are any data exceptions. Such data exceptions include, for instance, claims that are missing required values, claims that contain invalid codes, claims that contain non-sensical, coded combinations and types of claims for which the system has not previously identified baseline, minimum and maximum cost of the associated procedures. While most of these data exceptions can be tested for using conventional techniques, it is noted that it has been found useful to use a grouper to validate coded combinations, such as CPT and ICD codes. When the grouper is used in this manner, a dummy group of new claims is made and codes within the dummy group are reviewed to determine if the codes therein are valid. Claims for which there are data exceptions are also removed, as shown by the halt step 205 for those claims, so that they can be individually reviewed and the necessary data associated therewith added.

Either using all of the claims that have passed through the data exceptions test step 204 but, more preferably, using claims that have been corrected so that they now will pass through the data exceptions step 204, step 208 is used to identify new providers 20. As shown in the claim data that is provided and shown in FIG. 3A, there is an entry for a particular provider 20 that is associated with each claim. This provider may be the physician who is determined to be the responsible physician for this episode of care, as will be described hereinafter, or may also be a different physician or provider that has ordered tests or procedures for this patient as a result of this episode of care. In any event, step 208 identifies any new providers so that the incentive administrator database can be updated to take them into account.

Once new providers have been identified, step 210 follows, which will check for gaming as described hereinafter. In essence, gaming is a term commonly used to describe conduct in which any system is manipulated by providers to increase their monetary reward. Once gaming has been checked and has been identified, the claims data is adjusted based upon preprogrammed logic rules, as will be described hereinafter in FIG. 6A-3. After these logic adjustments have been made in step 230, adjustments are made for previously closed episodes in step 250. These adjustments for previously closed episodes will be described hereinafter in FIG. 6A-4.

Turning again to step 210, as described in FIG. 6A-1, FIG. 6A-2 illustrates in more detail the gaming check that takes place. As shown, in step 212, each new claim is received and, in step 214, it is determined whether there is an entry for the claims procedure and diagnosis codes in the "non-allowed table." By "non-allowed table" is meant a table contained within the incentive administrator's database that associates procedure codes with non-allowed diagnosis codes. For example, the diagnosis may be that a patient has broken a leg, and a permitted procedure is to order an X-ray, but a non-permitted procedure would be an CT Scan. Accordingly, within the non-allowed table, there exists the non-allowed pair of the procedure code for the broken leg, coupled with the diagnosis code for the CT Scan. Thus, any claim that is processed by the system that contains this combination of procedure code and diagnosis code will not be allowed. Accordingly, if such a claim is found, step 216 marks that claim as non-allowed and then continues to step 218 to determine if there is another claim that needs to be pre-processed in this manner. If such a claim exists, that claim is input in step 212 and the steps previously recited continue. If there is no other claim, then this gaming check that took place in step 210 is finished, and step 230 follows thereafter.

Figures 3, 6A:
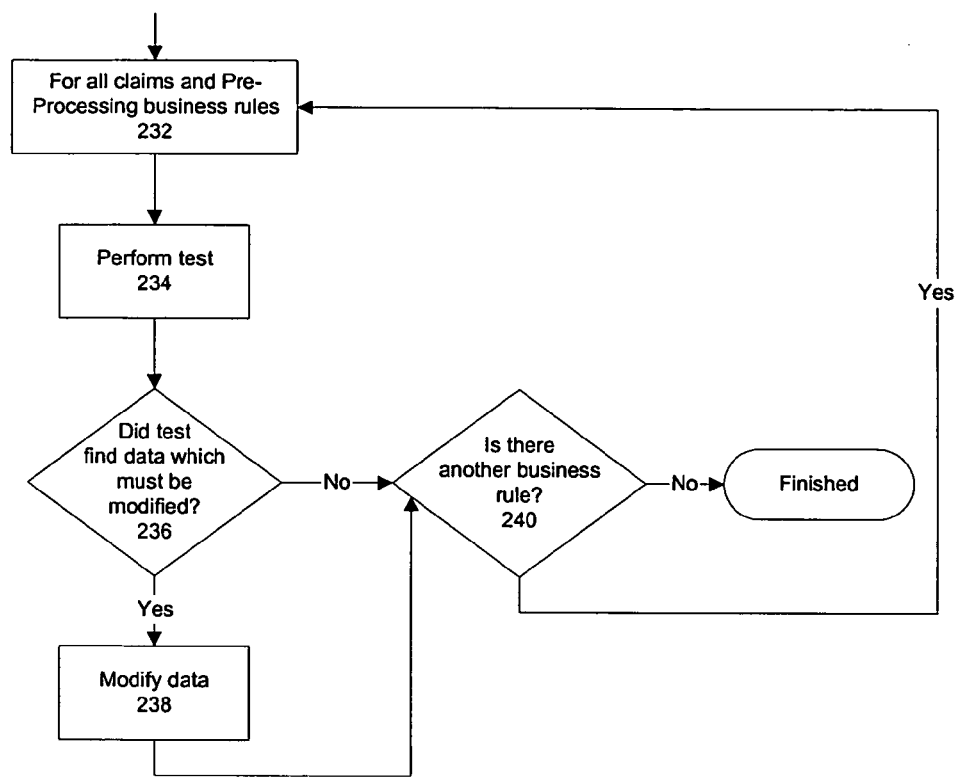
Figures 4, 6A:
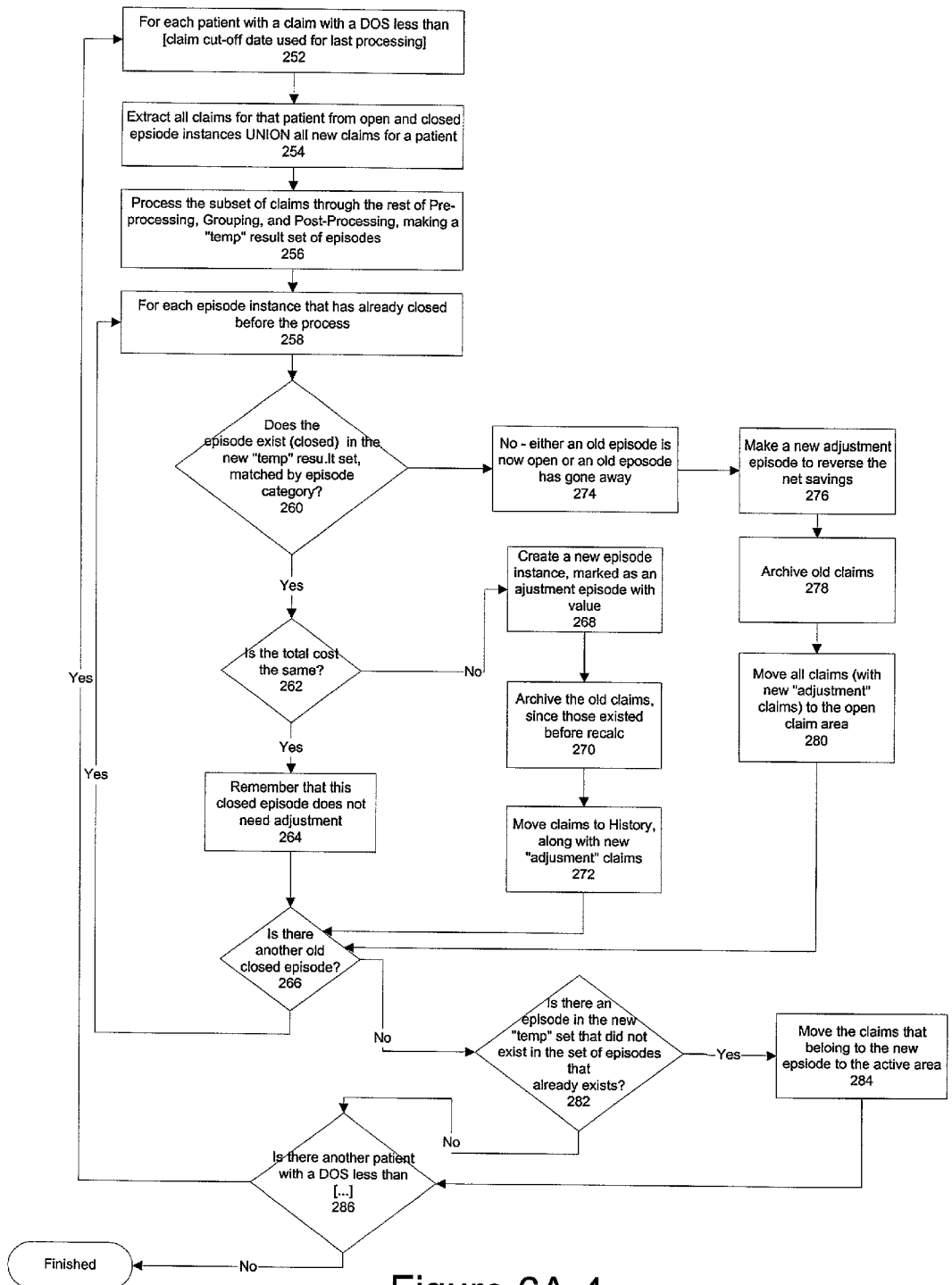

FIG. 6A-3 illustrates in more detail the logic adjustment that takes place in step 230. As illustrated, each of the claims is preferably operated upon by each of the business rules or logic adjustments that the system contains. Thus, they are input and then, in step 234, the business rule test is performed thereon. This test is preferably implemented via an AI Rule Engine. There can be as many as desired, or as few as desired, business rules that operate upon the data. Specifically, these logic adjustments are intended to make the claim data more accurate. For example, a cord PH test is one that is performed on newborn infants. However, when an infant is born there may not be a separate record in the hospital's billing system for the newborn infant and, as a result, the cord PH test can be attributed to the mother. A business rule can be generated that recognizes the miscoding of this test and automatically finds the infant within the system or creates a new claim for the infant, thereby recoding the claim for the infant rather than the mother. While the above is just an example of such a business rule, there can be many others that are implemented in an effort to make the claims data more accurate.

Step 236 illustrates the decision of whether the step 234 test found any data that requires modification. If so, step 238 follows and the modification to the data is made. In the example previously given, changing the coding from the mother to the infant would be the modification of the data within step 238. Step 240 follows, and determines for that claim whether there is another business rule that needs to be applied. If so, the steps previously described are implemented for that new business rule and, if not, then the pre-processing of logic and adjustments is completed.

Thereafter, as illustrated in FIG. 6A-1 at step 250 and in FIG. 6A-4 in more detail, a step of adjusting for claims that refer to previously closed episodes occur. Obtaining such a claim can occur, for instance, if there is a delay in transmitting the claim to the payor, if an episode of care was in fact completed, but a physician billed for care that was provided months after providing the care, or if an episode of care were closed, but there were reasons that it should not have been which were not detected or detectable at the time the episode was closed.

Such situations are dealt with in the present invention, and FIG. 6A-4 provides a preferred manner of dealing with them. As illustrated, in step 252, each claim is reviewed to determine if there is a date of service (DOS) that is earlier than the claim cut off date used in the last processing. For each such claim that exists, the following steps and decisions are made. Initially, in step 254, all the open and closed claims for that patient are added to the new claims that have been received. Then, in step 256, this subgroup of claims for this single patient are processed through the preprocessing step 200, the grouping step 300, and the post-processing step 400 as described previously and hereinafter, and a temporary result set of episodes is determined.

Thereafter, a determination is made of each previously closed episode in step 258, and for each such episode the following steps and decisions take place. In step 260, a decision is made whether in the temporary result set the same closed episode exists as had existed prior to this new batch of processing. If it did, then step 262 follows and a determination is made whether the overall cost of this episode is the same. If it is, then that previously closed episode does not require adjustment, as noted by step 264, and then step 266 follows, which will be described hereinafter.

If, in step 262 the total cost is not the same, then step 268 follows and an adjusted episode instance is created, which is marked as an adjustment to a previously closed episode, and a value of the adjustment is determined. This adjustment to value is made using the new claims data, based upon the calculations for incentive payments as described hereinafter. This adjustment is described within the logic of this process at this time since the adjusted episode remains closed, but of course could be determined with the other open claims that are then subsequently closed. Once the adjusted episode instance is created, then the claims as they existed before the recalculation are saved in step 270. This is done for record-keeping purposes so that the system can determine why it had previously made incentive payments, as well as determine the new adjustment to that previously made payment based upon the new claim or claims. Thereafter, in step 272, both the newly made adjusted episode instance claims, and the previously made closed episode instance claims are archived, and step 266 follows, as will be described hereinafter.

Referring again to step 260, if in step 260 it is determined that there is not a closed episode in the temporary set that matches a previously closed episode, then this means, as shown by step 274, that the previously closed episode should have remained open, or it should not have existed. An episode should not have existed, for example, if the episode was previously closed based upon one diagnosis, but the later claims now show that earlier diagnosis to be incorrect, and thus all of the claims need to be recalculated for that new diagnosis. As a result, step 276 follows and a new adjustment episode is made, which causes a reversal of the previously closed episode, including any incentive payments made. Thereafter, the claims related to the previously closed episode are archived in step 278 for record-keeping purposes so that the system can determine why it had previously made incentive payments. Step 280 follows thereafter and all of the claims are then moved to the open claim area so that they can be together operated upon as new open claims and step 266 follows.

Step 266, mentioned above, and subsequent steps will now be described. As shown, a determination is made whether there are any other previously closed episodes. If there are, then for each of those, step 260 and the steps that follow as described above follow. If there are no previously closed episodes, then step 282 follows and a determination is made whether there is a new episode in the temporary set that did not previously exist. If there is a new episode, then step 284 follows and all of those claims are moved to a newly created episode instance and then into the open (active) data set previously referenced at step 100, so that they can then be processed with the remaining steps as described hereinafter, and then step 286 follows. If there was not a new episode determined in step 282, step 286 follows directly.

In step 286 it is determined if there is another patient with a date of service that less than the processing cut-off. If there is, then step 252 and the steps following, as described previously, are performed for each such patient and service. If there are none, then the adjustments to closed episodes step 250 is completed, and the process moves on to the grouping step.

Once all of the pre-processing of claims data has been completed, as illustrated in FIG. 5 by step 200, then this data is grouped into various episodes of care in step 300, which will now be described with reference to FIG. 7. The grouping step is shown as a discrete step from the preprocessing step 200 and the post-processing step 400 since, in the preferred embodiment, the grouping step 300 uses the Episode Treatment Groups grouper that is made by Symmetry Health Data Systems of Phoenix Ariz. While the present invention can be implemented using any grouper and other application software or systems that result in episode payment groups (EPGs), at the present time using this Symmetry grouper to establish episode treatment groups (ETGs) that can, in turn be used to establish episode payment groups (EPGs) as will be described hereinafter, has been found effective. Thus, the preprocessing as previously described and post-processing as subsequently described takes into account the use of this grouper, but the present invention is not limited to being implemented with this grouper, but could be implemented with other systems that can group into payment grouping episode categories, directly or indirectly. It should also be noted that this grouper is being used in the present invention in a manner that is different that the typical use of providing normative information. Thus, the manner in which the grouper is being used will be described in some detail.

Figure 7:
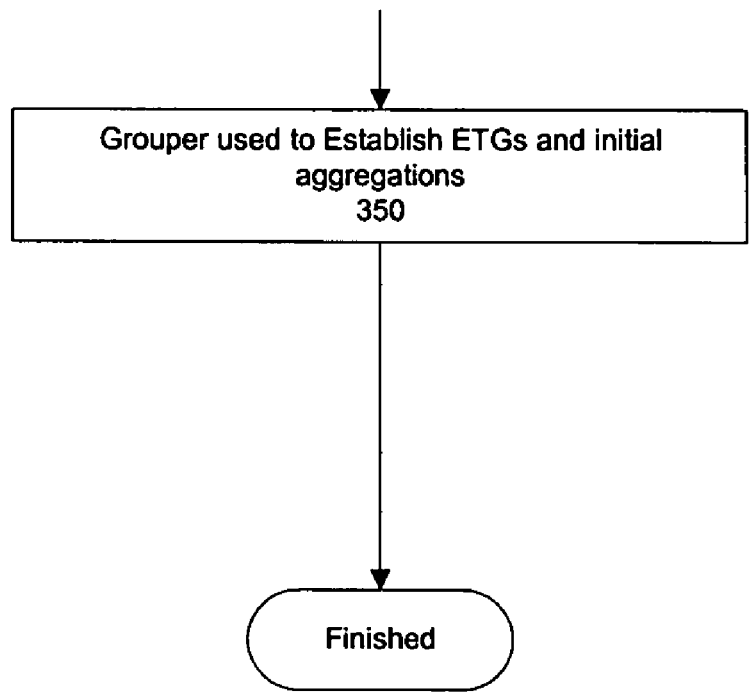
FIG. 7 illustrates a flowchart of grouping claims data according to the present invention.

As illustrated in FIG. 7, the grouping step 300, shown more specifically as step 350, performs an initial aggregation of claims to form episode clusters that can then be aggregated into episodes, as well as to obtain record types for each claim to designate the category of expense.

With respect to forming episode clusters, the grouper determines, for each patient, which claims to aggregate, and ultimately assigns the Episode Treatment Group (ETG) code to each such episode. This is the standard process that the grouper conventionally performs. Along with the ETG code that is assigned there is also assigned an episode type flag, which is a code that assists in indicating the degree of confidence in the accuracy of the episode instance. The episode type flag code signifies a number of different types of characteristics of the episode being analyzed, but among the characteristics, the episode type flag code allows for the determination of whether the episode is closed or open. Thus, the episode type flag code can indicate, among other things, whether an episode is should be categorized as being completed, or closed, or still open.

Further, the claims data is analyzed so that each different claim can be attributed to a type of expense. Expenses are divided into categories, including categories for management expenses, pharmacy expenses, in-service hospital expenses and ancillary expenses. Claims classified by the grouper as management expenses have a correlation with the costs incurred by a physician at his office in treating a patient. Accordingly, while others manner of correlating costs incurred by physicians for treating patients in their office can be used, this information supplied by the grouper has been found useful in determining the responsible physician, as will be described hereinafter.

Further, as described above, the grouper is used as part of a cycle of data analysis. As described previously in step 600, after an initial preprocessing, grouping, and post-processing, the grouped data is reviewed for errors. If there are any problems, the problems are edited, and then the preprocessing, grouping and post-processing is performed again. This process repeats until there are no problems that remain to be edited. Regrouping the same data a plurality of times is not conventionally performed, since the manner in which the grouped data is conventionally used is much different than in the present invention.

Thereafter, once the data has been grouped into episodes of care in step 300, as illustrated in FIG. 5, the post-processing of grouped data takes place in step 400, which will now be described with reference to FIGS. 8A-1 through 8A-4.

Figures 1, 8A:
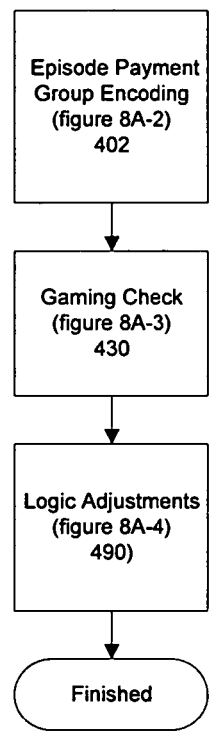
Figures 2, 8A:
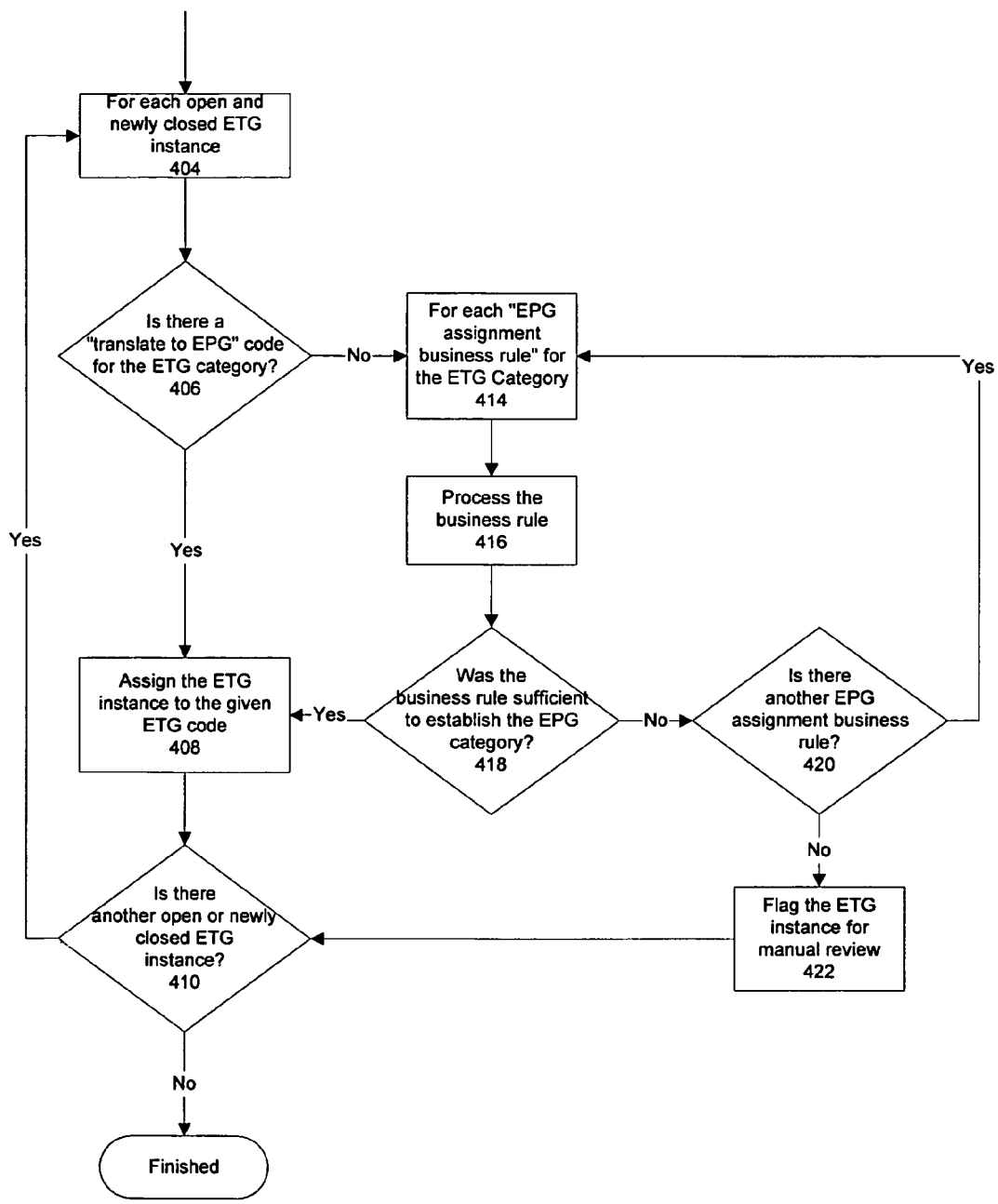
Figures 4, 8A:
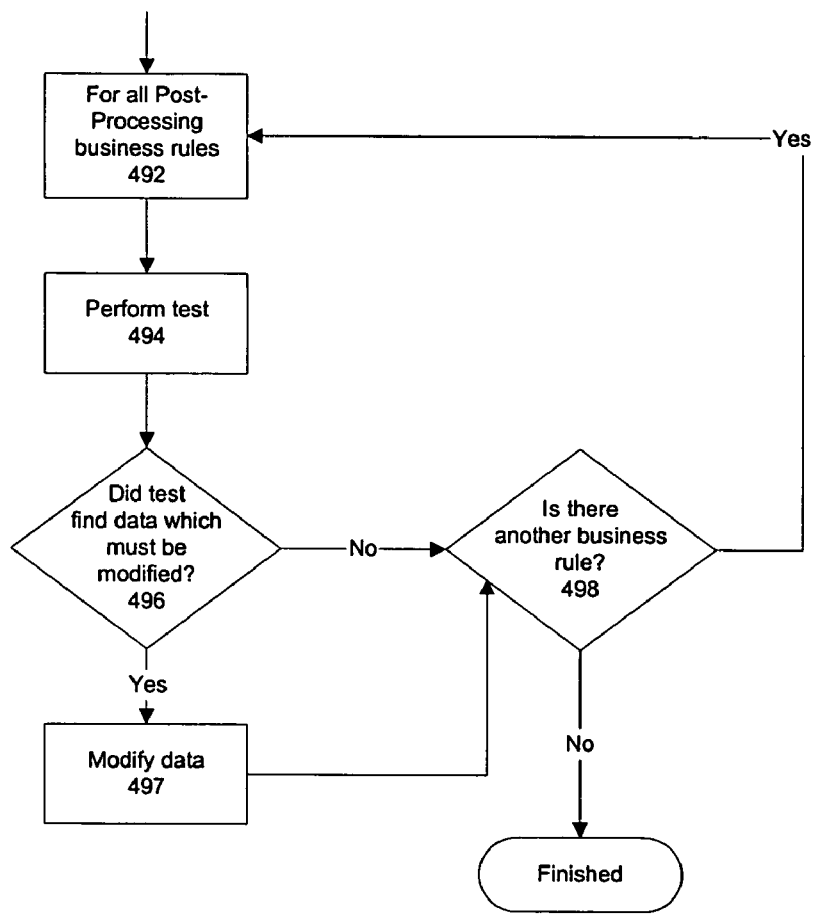

FIG. 8A-1 illustrates the overall steps that take place in the post-processing of the grouped claims data, as shown. In step 402, Episode Payment Group (EPG) encoding takes place. Thereafter, further gaming checking takes place in step 430, and, in step 490, further logic adjustments take place. Each of these will now be described in more detail.

The episode payment group encoding step 402 is, in general terms, providing an additional level of detail to conventional claims data. In particular, as illustrated in FIG. 3A-2, claims data that has been grouped will contain what has been described above and is known as an ETG instance classification. An ETG instance classification classifies that claim as one of approximately 580 specific types of ETGs. While the episode treatment groups as conventionally used have functionality within the context that they were originally created, they are different than EPG in a number ways. The primary differences being that certain ETG groups are more properly grouped as a single EPG, and certain ETG classifications are more properly grouped into a number of different EPG classifications.

It is nonetheless possible, though not preferred, to use the ETG classifications and not translate them to the EPG category discussed hereinafter and still obtain certain of the advantages of the present invention. As a result, it should be apparent that EPGs are a logical construction which represent normative and actual aggregations of medical claims into a single unit that is both clinically and financially relevant. The emphasis is on the payment, seeking to determine a categorization of the payments for the actual treatment in comparison with a norm for the actual condition.

The translation to an EPG, whether made from an ETG or using some other manner of grouping, should, however, aggregate conditions that are similar in both fact and appearance, because the EPG measure seeks to be comparative against a clinical/financial norm.

As an example, whereas there is only a single ETG for osteoporosis, it may be determined that there should be multiple EPGs since, in the presence of different comorbidities, the average treatment cost could be very different.

As another example, though there are two different ETGs for a fungal skin infection, one for a condition that requires surgery and another for a condition that does not require surgery, it would typically be determined that there should be only a single EPG. This is because the ETG for the infection with surgery assumes that surgery was needed, but under the constructs of the present invention that is an assumption that would be avoided. Though the ETG categorization indicates that the surgery occurred, it cannot provide any insight into whether the surgery was necessary or could have been avoided. Thus, having a single EPG, which could then be adjusted for comorbidities that will then indicate that circumstances warranted the usage of surgery.

And an example of a single ETG that maps to more than one EPG are claims from a patient for both birth control pills and seratonin based medication that could both map to the ETG category for a routine exam. Since, however, the birth control pills are more properly associated with a wellness and maintenance episode relating to reproductive health, and the seratonin based medication is more properly associated with a wellness and maintenance episode relating to psychiatric health, separate EPGs for these different wellness and maintenance episodes would exist.

Accordingly, with the above description in mind, FIG. 8A-2 illustrates that, for each open and newly-closed ETG instance ("instance" is also used to refer to episode of care) in step 404, step 406 follows and a determination is made whether there is a EPG category for the ETG category so that a direct translation can be made. If there is, step 408 follows and, for each claim associated with that instance, the EPG category is then associated with it. Thereafter, in step 410, a decision is made as to whether there is another open, or newly-closed ETG instance that needs to be operated upon and, if so, that is done. If not, then the episode payment group and coding process is completed.

However, if, in step 406, a determination is made that there is not a direct translation for the ETG category to a EPG category, for each instance, then a number of EPG category assignment business rules are used to determine the correct translation. This is illustrated in step 414 that identifies the existence of these EPG category assignment business rules and, in step 416, operates upon the claims data, using the business rule to determine if a EPG category can be found. These business rules are obtained based upon logic associated with the various types of episodes such as provided in the above-mentioned examples where a direct translation from an ETG to a EPG category did not occur. Step 418 determines whether this EPG category was found and, if it was, then step 408 follows with the steps, as described thereafter, following thereon, using that EPG code. If the business rule was not sufficient to establish the EPG category, step 420 determines if another business rule exists that would potentially allow the categorization of the ETG category into a EPG category. If it does, then that business rule is identified in step 414 and the steps previously recited follow. If not, step 422 follows and this particular claim is flagged so that the ETG instance can be reviewed manually, and a determination of the EPG category made. Once this manual review is completed for each of the claims, there will then be a EPG category associated with each of the instances. It is noted, of course, that open data 100 that had been previously operated upon may contain a EPG category and, to the extent that certain instances already contain such a category, those instances need not be operated upon again, although new claims associated with that instance can be so categorized.

Following the episode payment group encoding, a further post-processing gaming check step takes place, as identified in FIG. 8A-1, as step 430. Step 430 can contain various further gaming checks, four of which are identified in FIG. 8A-3. These four various gaming checks are checking for serial episodes (430A), checking for costs that are too low, referred to as floor analysis (430B), checking for diagnosis upcoding (430C), and checking for the need to prorata partial episodes (430D). Each of these will now be discussed. It should be noted, however, that while all of the various gaming checks described herein are preferably implemented, that all, none or some of them can be implemented, as well as others. Furthermore the order in which they are performed is not significant to the implementation of the present invention.

In the check for serial episodes (step 430A), step 432 begins the process in which each EPG instance is operated upon and step 434 makes a query as to whether the same patient had an earlier instance of the same, or similar, EPG category. Similar EPGs are determined in an instance table within the incentive administrator database 40 that associates EPG categories that are related. Thus, if there were an earlier instance of a related EPG category, step 436 follows and a determination is made if this were a chronic condition. If it is a chronic condition, and would thus require repetitive visits to the provider 20, step 438 follows and it is determined whether there is another instance to check and, if not, then the analysis of step 430B continues. If there is another instance to check, the steps, as previously described and further subsequently described hereinafter, take place.

If, in step 434, it is determined that there was not an earlier instance of the same or similar EPG category, then step 438 also follows since there is not the possibility of there being a serial occurrence of these kind of events.

If, however, in step 436, it was determined that the condition is not chronic, step 440 follows and prior episodes of the EPG categories are reviewed, and the most recent instance is selected. Thereafter, in step 442, a determination is made regarding the number of days between the start date for this particular EPG category instance (referred to as the "main" episode), and the prior episode's end date. If the number of days between episodes is less than a predetermined number of days that is not suspicious for this EPG category, then this main episode is flagged in step 444 for subsequent review. This is because this determination signifies that the claims now associated with this main episode may, in fact, have been part of a previous episode of care. If such were the case, then credit should not be given to the provider 20 for a second episode of care but, rather, the claims now attributed to the main episode should be attributed with the previous episode of care having the same EPG category. Accordingly, flagged main events will not be used in the determination of an incentive payment based upon a new episode of care.

If, however, in step 442, the number of days determined is greater than the number of days between the episodes which is not suspicious value, then step 438 follows and the steps as described hereinafter ensue. Accordingly, this completes the check for serial episodes.

Following is the floor analysis determination step 430B. This begins with step 446 for each newly-closed EPG instance and the determination in step 448 as to whether the "override floor baseline" indicator has been set for this EPG instance. Each EPG category has a minimum value previously established. To override this minimum value, the override floor baseline indicator is set to signify that it has been previously determined that, although the amount for this EPG instance is below a baseline floor minimum value for the category, that that is acceptable because it has been previously been investigated. If, however, the override floor baseline indicator has not been set, step 450 follows and a determination is made whether the adjusted baseline for this newly-closed EPG instance is below the floor-base line value for this EPG instance. If it is then, in step 452, this episode of care is marked as being below the floor baseline so that it can be further investigated thereafter. If, however, in step 450, the adjusted baseline is not below the floor baseline value, then the record is not so-marked. In either event, step 454 follows, and a determination is made as to whether there is another newly-closed EPG instance to operate upon. If so, that is done using the methodology previously discussed. If not, then the diagnosis upcoding step 430C follows.

Diagnosis upcoding step 430C checks for the existence of diagnoses that are more severe than the actual condition that the patient has. Diagnoses of this type can, as explained previously, allow the provider 20 to receive greater compensation than the provider is entitled to. Accordingly, to check for diagnosis upcoding, for each newly-closed EPG instance, as shown in step 456, there is initially a check in step 458 to determine whether an override diagnosis upcoded check indicator has been set for this EPG instance. If the override indicator has been set, similar to the override indicator in the floor analysis discussed previously, step 460 follows and it is determined whether there is another newly-closed EPG instance to operate upon. If, however, in step 458, the override diagnosis indicator has not been set, step 462 follows and, for that EPG category, the associated upcoding diagnosis check tests are then run. The first such test is ran, as illustrated in step 464, by the execution of the related test, which follows in step 466 with the determination of whether a result set was found. If a result set was found, the episode is marked as a possible diagnosis upcode in step 468. Thereafter, step 470 follows to determine if there is another test for this category. If there is, then that test is input and step 464 is repeated and the steps, as described, follow thereafter. Once all of the tests have been completed, it can be determined whether there is a possible diagnosis upcode for this EPG instance.

The upcode diagnosis check tests in step 462 for each EPG category again use the AI Rule Engine that has been previously discussed. Any number of such rules can be made to determine whether there is the possibility of upcoding. For example, if a patient comes to a provider 20 with a common cold, which is diagnosed as pneumonia, the totality of claims data is checked for that episode of care to determine whether drugs characteristic to the treatment of pneumonia were, in fact, administered. If they were not, then the fact that none of these drugs were prescribed can be used to create one of the upcode diagnosis check tests for instances of this particular EPG category.

After the diagnosis upcoding takes place from step 430C, then the prorata of partial episode step 430D takes place. In this step, it is generally being determined whether the patient submitting the claim is still part of the plan that is associated with the payer 30. A person may voluntarily leave a plan to go join another plan from a different payer or, alternatively, may have passed away. Accordingly, for partial episodes, a factor is needed to determine a partial incentive payment.

As shown in FIG. 8A3 relating to step 430D, step 472 begins by determining whether the payer has provided a list of members who have exited the plan. If no such list exists, then this step cannot be performed and it is skipped. If such a list has been made, step 476 follows and, for each patient who has exited the plan before a claims cutoff date used in the processing, a determination is made, as shown in step 478, of whether the patient has any open episodes. If there are no open episodes, a determination is then made in step 480 as to whether there is another patient who has exited the plan for the claim cutoff date used in the last processing. If so, then the steps described both previously and subsequently with respect to determining a prorata partial episode factor are made. If, however, in step 478, the patient does have an open episode, for each open episode, as illustrated in step 482, step 484 determines the average length of the episode with the same EPG category in the files of closed episodes, and then, in step 486, determines the factor to use based upon the information previously obtained. Step 486 entails calculating the proposed baseline override value for the open episode to the adjusted baseline, multiplied by the ratio of the actual length of the open episode, which is multiplied by the mean calculated in step 484. As a result, a factor (or prorata percentage) for the partial episode is determined that can be used in the subsequent calculation of determining an incentive payment for the physician or provider.

After step 486, step 488 follows to determine whether there is another episode open for this patient. If so, steps 482 through 486 are repeated and, if not, step 480 follows and is implemented as has been described. Accordingly, the post-processing game checking of step 430 is, thus, complete.

Accordingly, post-processing logic adjustments of step 490 then take place. These are described in more detail in FIG. 8A-4. Post-processing logic adjustments, similar to the preprocessing logic adjustments described, contain a set of all the post-processing business rules, as indicated in step 492. For each business rule, the EPG instance is operated upon in step 494 and step 496 determines whether the AI Rules Engine test found data that required modification. If so, that data is modified in step 497 with step 498 following thereafter and, if not, step 498 follows directly. In step 498, it is determined whether there is another business rule and, if so, that business rule is operated upon in a subsequent repetition of step 494 and steps following thereafter. If not, then the post-processing logic adjustments are completed.

An example of a post-processing logic adjustment is the existence of a chronic condition in which the patient has not seen the provider 20 for period of time that exceeds the predetermined window, thus causing the grouper in step 300 to close the episode, as has been previously described. If, however, the chronic condition is one that requires the continued refilling of a prescription, such as an inhaler for an asthmatic, then the post-processing logic adjustment can have a rule that looks for closed cases of asthmatics and artificially keeps them open so that the claim for the prescription can be processed.

After the post-processing logic adjustments, the step of determining the responsible physician can be made. As noted above, the determination of a responsible physician, illustrated in FIG. 5 at step 500, can take place earlier in the process, in fact at any time after a EPG instance has been identified. However, for sake of convenience, it is discussed at this point. Prior to discussing in detail the automated steps that the present invention uses to determine a responsible physician, it is noted that this process is needed in order to determine the specific physician who will receive any incentive provided according to the present invention. This is significant since, while in an episode of care, a patient may see any number of different physicians or providers, there is typically a single physician or provider who causes the involvement of other physicians or providers and is thus most responsible for the overall cost associated with the episode of care. Accordingly, by determining which physician or provider is the one primarily responsible for the other physicians and providers actions, the present invention specifically attributes an incentive award to that physician who is responsible for making those decisions. Accordingly, this method of determining a responsible physician was useful both within the context of the present invention as well as in other contexts where it is helpful to know whom the responsible physician should be.

Figures 1, 9A:
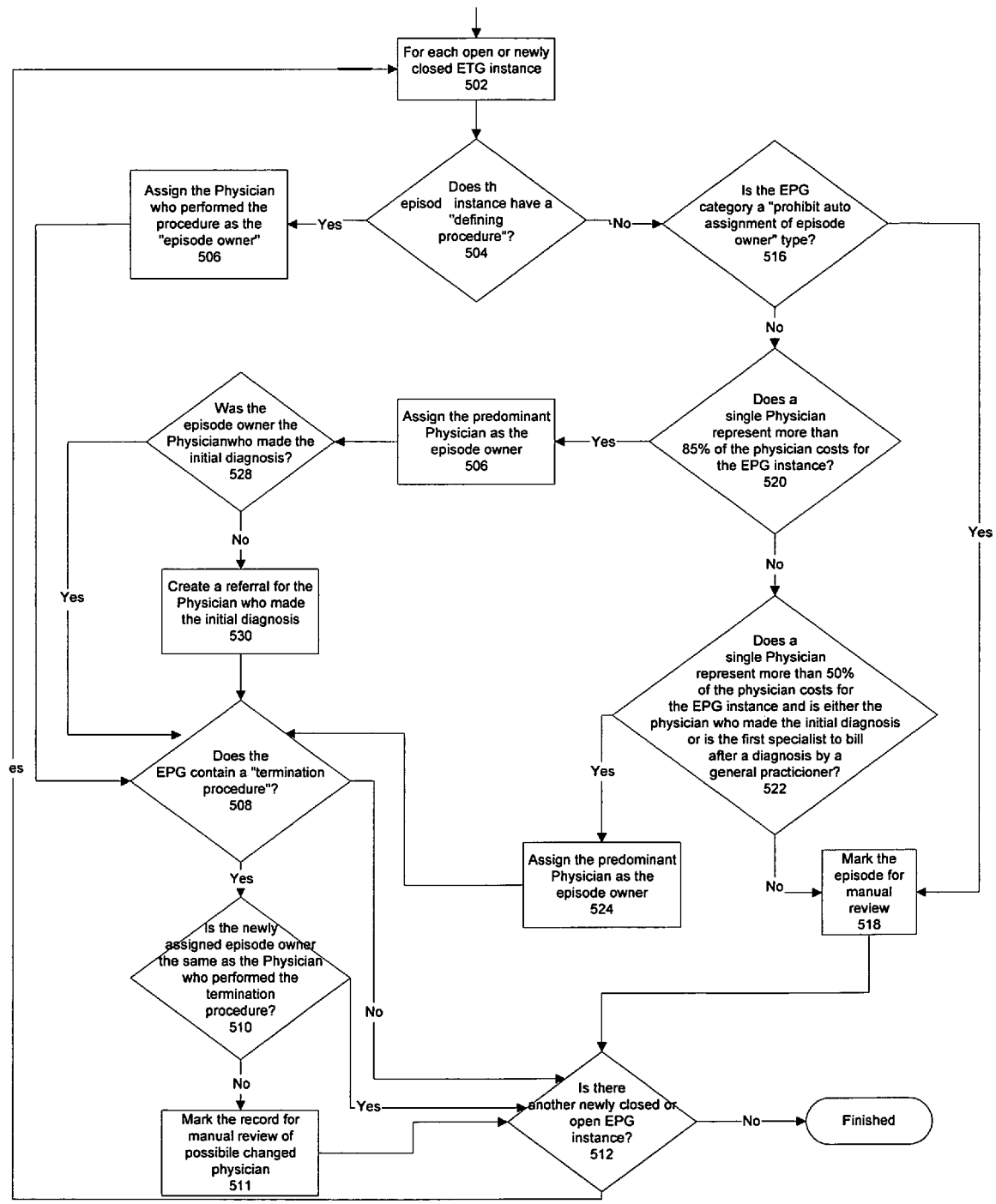
Figures 2, 9A:
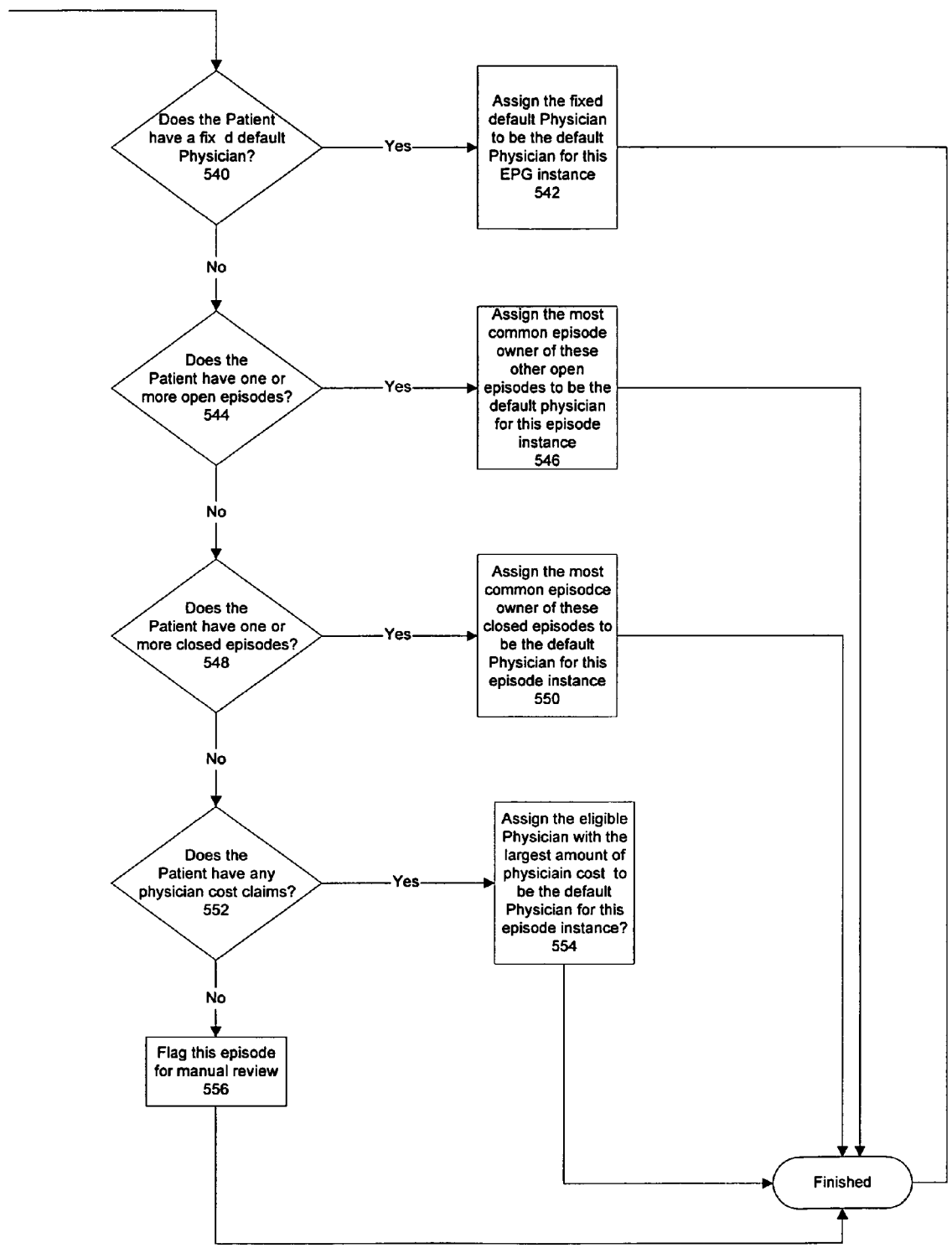

As illustrated in FIG. 9A-1, for each open or newly-closed EPG instance, as illustrated by step 502, step 504 determines whether the episode instances as a "defining procedure." Examples of defining procedures are major surgeries or, in the context or pregnancy, a delivery. If, for the episode instance, there is a defining procedure, then the physician who performed the procedure is defined as the episode owner in step 506. The episode owner is likely to be the responsible physician, but, in step 508, a subsequent check is made to determine whether the EPG instance contains a "termination procedure."

For most procedures, the provider who performed the defining procedure will be the same person who performed the termination procedure, but this may not always be the case. For example, in a bone marrow transplant, the harvesting of the marrow may be the defining procedure, but the restoration of the bone marrow might be the terminating procedure. If these were done by different physicians, that may be evidence that the responsible physician has changed during the course of treatment. Thus, in step 508, if there is a termination procedure involved, in step 510 a determination is made as to whether the physician who performed the defining procedure is the same as the one who performed the termination procedure. If not, step 511 is performed and the new provider is also noted on the EPG record so that the incentives payments can be split in some manner between the provider who performed the initial defining procedure, and the subsequent defining procedure. If, however, they are the same, then step 512 follows and a determination is made as to whether there is another newly-closed, or open, EPG instance that needs to be operated upon in a manner that uses the steps as described both previously and subsequently.

Previously, with reference to FIG. 9A-1, there has been described how to determine the responsible physician if there was a defining procedure, as was initiated by the determination made in step 504. If, however there is not a defining procedure, step 516 follows and the determination is made as to whether this EPG category is of the type that does not allow the automatic assignment of an episode owner. If this EPG category is of that type step 518 follows and the EPG instance is marked for manual review. An example of such a EPG category that does not presently allow for automatic assignment is a category in which a number of physicians, and not just a single physician, are typically involved. A specific example of this would be a cancer patient who will have many different physicians involved in determining how to proceed with the case.

If, however, in step 516, it is determined that this EPG category is not of a type that prevents auto assignment, then step 520 follows in which it is determined whether a single physician is the cause of more than 85% of the physician costs for the EPG instance. By physician costs is loosely meant costs incurred as a result of the physician or his staff treating the patient, in contrast to another facility treating the patient or lab tests by another entity being performed. If a single physician is responsible for more than 85% of those costs, that physician is made episode owner in step 506 and then step 528 follows to determine whether this physician was the physician who made the initial diagnosis. If the answer is yes, then the step 508 follows. If the episode owner was not the physician who made the initial diagnosis, step 530 follows and a referral is created for the physician who did make the initial diagnosis. This referral is used for purposes of providing incentives to referring physicians, as will be discussed hereinafter. In any event, if a referral for referring physician is created in step 530, step 508 still follows and it and the following steps are executed as described above.

If, however, in step 520, it is determined that there is not a single physician who is responsible for incurring more than 85% of the physician costs for the EPG instance, step 522 follows. A determination is made in step 522 as to whether there is a single physician who represented more than 50% of the physician costs and was either the physician who made the initial diagnosis or was the first specialist to bill the patient after diagnosis by a general practitioner. If the answer to the query in step 522 is yes, then that physician is assigned as the episode owner in step 524, and step 508 follows. If, however, a physician still cannot be identified as a result of the test in step 522, then that EPG instance is marked in step 518 for manual review. It is noted that if the Symmetry grouper is used, that the physician costs can be derived from claims that are designated as being of the management record type M, as discussed previously in the discussion of the grouper.

Accordingly, a substantial number of the EPG instances can be automatically identified without requiring any manual review. Even when a "manual review" is deemed necessary, a portion of that review can also be automated. As illustrated in FIG. 9A-2, a typical provider can be the default physician of the patient. Accordingly, FIG. 9A-2 illustrates a method for determining a default physician. This begins with a determination in step 540 of whether the patient already has a fixed default physician. If the answer is yes then that physician can be assigned as the default physician for this EPG instance. This default assignment can be manually reviewed if desired but, if not, that person can also be determined to be the responsible physician. If there was not previously a fixed default physician, then step 544 follows and it is determined whether the patient has one or more open episodes. If there are, step 546 follows and the physician who is assigned to the most common episodes for this patient is identified as the episode owner for this instance. If, in step 544, there are not one or more open episodes, step 548 follows and a determination is made as to whether there are one or more closed episodes. If the answer to that is yes, then, as in step 546, the most common episode owner of these closed episodes is assigned as the default physician for this particular episode. If, however, in step 548, there is not one or more closed episodes, step 552 follows and a query is made as to whether the patient has any physician cost claims, which, as described above, correspond to the management type record claims in the Symmetry grouper. If the answer to that is yes, the physician who has the largest amount of such claims costs is assigned to be the default physician for this particular episode instance. If not, then this episode is again flagged for manual review and can be assigned after manual review.

Returning again to FIG. 5, after the step 500 just discussed in detail, there follows step 610 that tests for closed instances, as previously described, and each closed instance is then operated upon, as summarized above in the discussion of FIG. 5. Certain of the details of those steps, as implemented in the preferred embodiment of the invention, will now be described.

Initially, the step 650 that tests for outliers, or extremes will be discussed. As mentioned above, the testing of outliers is performed in order to remove episodes of care that are extremes, and particularly extremes that result in costs that are much greater than the baseline determinations. Since the baseline values for different EPGs are based upon norms for that type of procedure, incentives are fairly calculated based upon procedures that have some similarity to the norms. And, while there will always be exceptions, for example due to a patient developing complications that are unforeseen, it would be unfair to penalize a physician for the extra costs incurred as a result of the complications and it would also be unfair to provide incentives based upon the extra costs incurred as a result of those complications.

Figure 10:
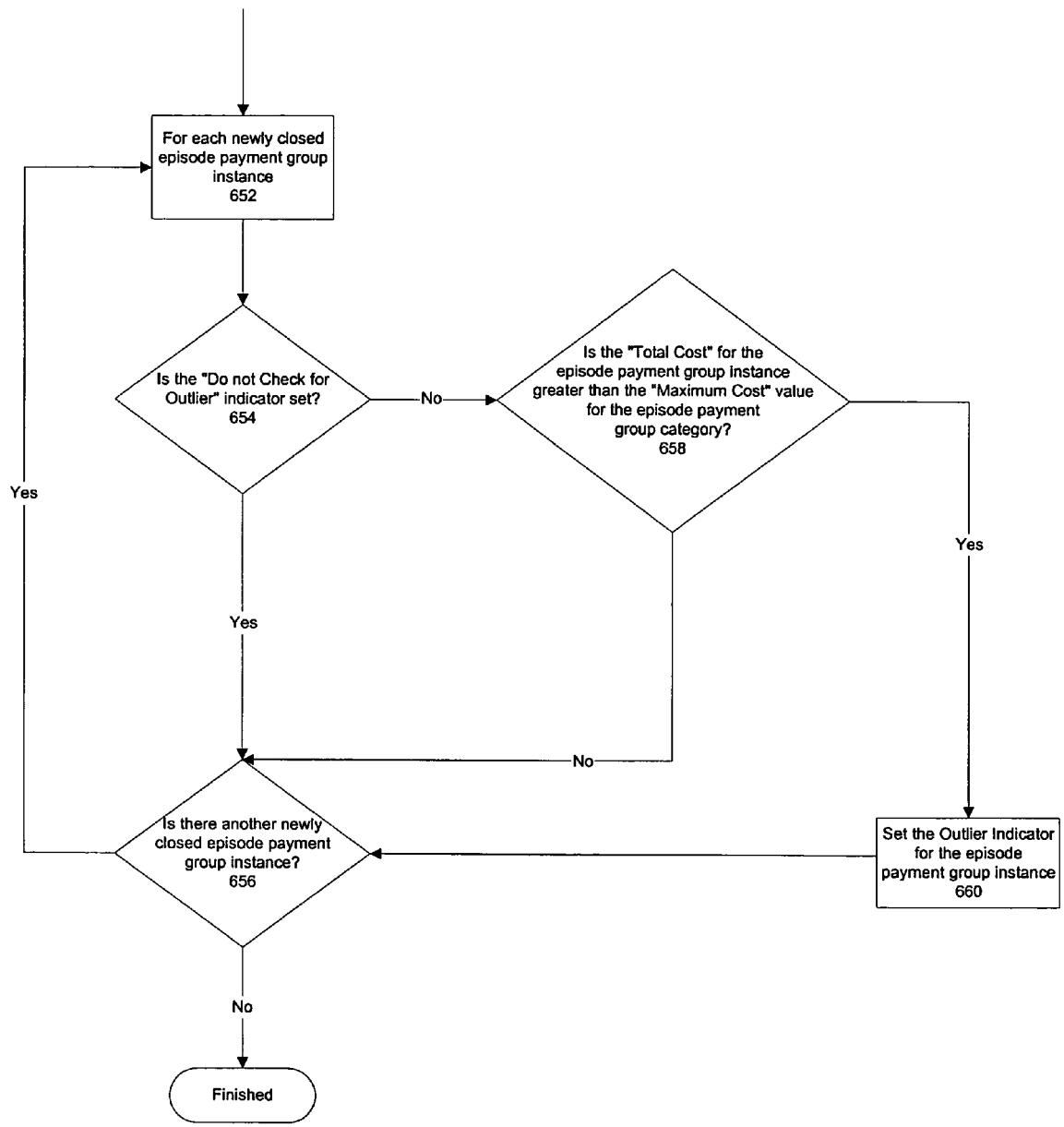
FIG. 10 illustrates a flowchart of outlier determination according to the present invention.

Accordingly, in testing for outliers, as shown in FIG. 10, step 652 acts upon each newly closed EPG instance, and queries in step 654 whether a do not check for outlier indicator has been previously set. This indicator will typically have been manually set, although the indicator can automatically be set for certain types of EPG categories. If the indicator is set, then step 656 follows and a determination is made whether there is another EPG instance that needs to be checked. If so, then steps as described above and hereinafter follow for that next instance, and if not then the outlier determination is complete.

If, however, in step 654 the indicator is not set, then step 658 follows and for that instance the total cost for the episode of care is compared against a predetermined maximum cost value associated with that type of EPG instance. If the total cost is not greater than the maximum, then step 656 as described above follows. If the total cost greater than the maximum, then step 660 follows and the outlier indicator is set. With the outlier indicator set, that allows for either a manual review of the episode, or, alternatively, the automatic treatment of the episode such that the incentive, if any, will be based on the predetermined maximum cost value rather than the actual cost. Other uses of this indicator are also possible.

After the outliers test 650 is complete, then the comorbidity adjustment 680 preferably takes place, in which, as described above, effects of one illness that can exacerbate or make easier the treatment of another illness are taken into account for purposes of altering the baseline for that EPG category, as well as altering the incentive factor. Thus, as shown in FIG. 11, each newly closed EPG instance is operated upon, although it is noted that open instances can also be operated upon if it is desired to provide an estimate of the baseline value adjusted for comorbidity to the responsible physician or provider.

Figure 11:
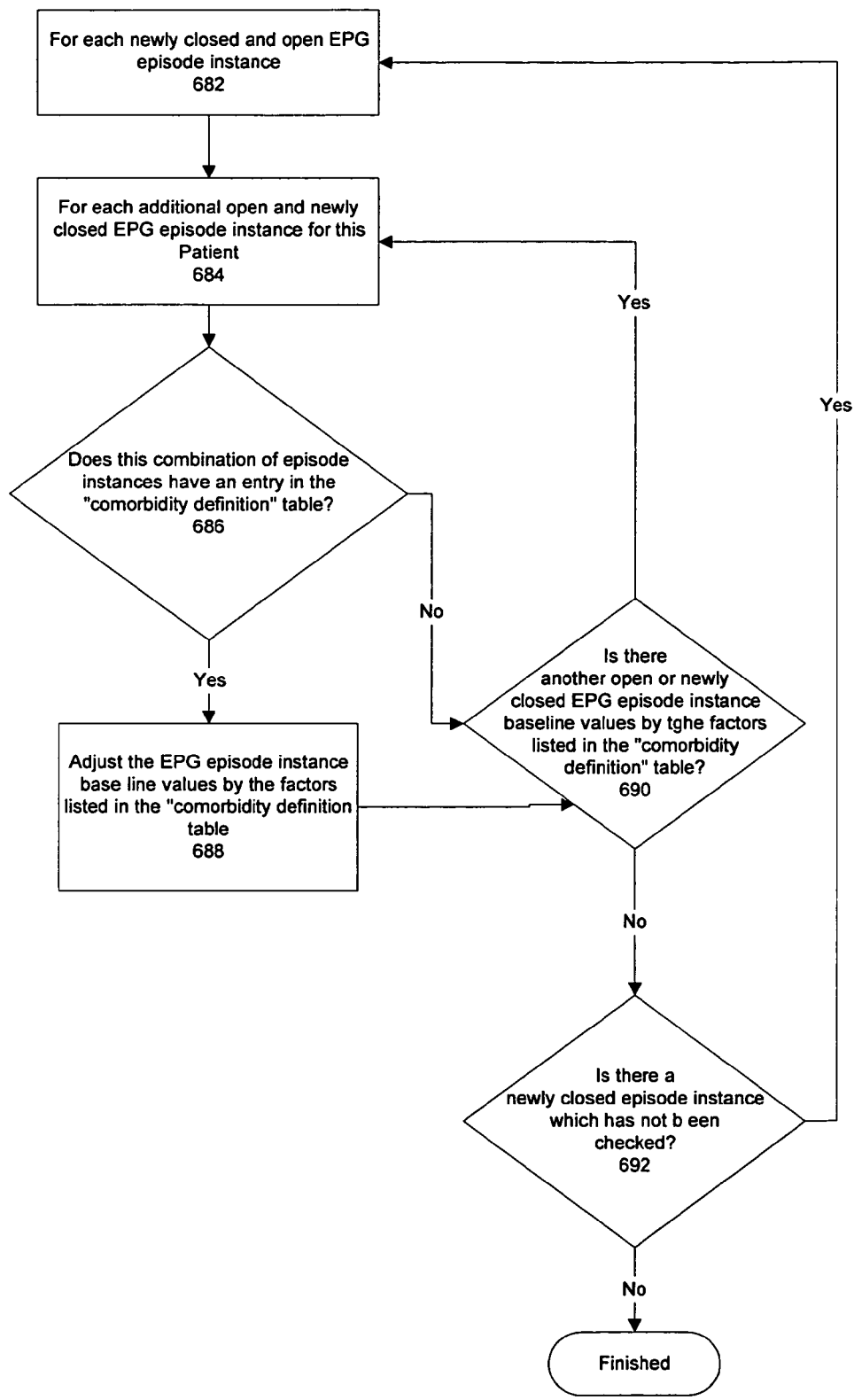
FIG. 11 illustrates a flowchart of determining comorbidity according to the present invention.

Step 682 of FIG. 11 is used to show each closed and open instance, which is then operated upon in step 684 to correlate open and closed instances for each patient, such that each correlation can be operated upon in step 686. In step 686 it is determined whether this combination of instances has an entry in a comorbidity definition table. If it does, then the baseline value of the EPG instance is adjusted to reflect the comorbidity factor. Thus, for instance, if a person is being treated for both asthma and bronchitis, which are two distinct episodes of care, the fact that there is an overlap of treatment for both may cause the baseline value for each to be only 70% of the typical baseline if only one of those episodes existed without the other. Further, for instance, if a pregnant woman is also being treated for hypertension, then the fact that this complicates the treatment of both could cause the baseline value for the pregnancy to be 170% as compared to a normal pregnancy, and the baseline value for the hypertension to be 140% as compared to a typical episode of hypertension.

If the pair of instances tested in step 686 do not have an entry in the comorbidity table, or if there is an instance which has thus been resolved in step 688, then step 690 follows and it is determined whether for that patient there is another pair of episodes that should be operated upon. If so, then step 684 and subsequent steps follow for that next pair of instances, and if not then step 692 follows and it is determined if there are any newly closed instances for another patient that need to be operated upon. If there is, then step 682 and subsequent steps as described above follow, but if there is not then the comorbidity determination is finished.

After the comorbidity determination, the calculate savings step 700 takes place, with the preferred manner of calculating savings being now further described with reference to FIG. 12. As illustrated, in step 702 each newly closed EPG instance, with the information obtained in the previously described steps, is operated upon. In step 704, a determination is made whether a do not pay incentive indicator is set. This can be set in many different manners. For instance, this indicator could be set if the serial episode gaming indicator or the possible upcode gaming indicator were set as described in previous steps. This do not pay incentive indicator could also be set based upon other considerations. If set, however, then a savings field associated with the episode is set to null, thereby indicating that there was no savings and thus no incentive should be paid, and step 208 follows to determine if there is another episode that needs to be operated upon, followed by either that operation as being described or the completion of the incentive payment calculation.

If, however, in step 704 the do not pay indicator is not set, then step 710 follows and all of the claims for the episode are totaled to obtain an total cost for this episode of care. With the total cost being determined, then step 712 follows to determine if an adjusted baseline amount exists. If it does not, then step 714 follows and a savings is determined by subtracting from the total cost the normal baseline value for that EPG type of episode of care. If the savings value is positive, then a savings has been realized and that value is used for incentive determination purposes as described hereinafter, whereas if the savings value is negative, then there has not been any savings realized.

It should be noted that the system can be implemented such that a negative savings value results in a net negative incentive for that episode of care, or can be implemented such that a negative savings value results in the savings value for that episode being reported as zero for that episode of care. The latter implementation has the advantage of reducing a provider's potential anxiety about implementing the system of the present invention in the first instance, since there is much less probability of there being a down-side to the program if there does not exist a net negative incentive for any episode of care. The latter implementation also distorts reality, however, in that incentive can get paid to providers who overall are inefficient. Accordingly, the savings value can be used in a variety of ways to balance the effect of the extremes mentioned above.

Regardless of the specific implementation, after the savings value is determined for a normal EPG baseline, then step 708 follows as described previously. If, however, an adjusted baseline exists, then this is determined in step 712 and operated upon in step 716, using the adjusted baseline value, but otherwise as described above. This adjusted baseline value can be adjusted for comorbidity, or a partial episode, as previously described.

Figure 13:
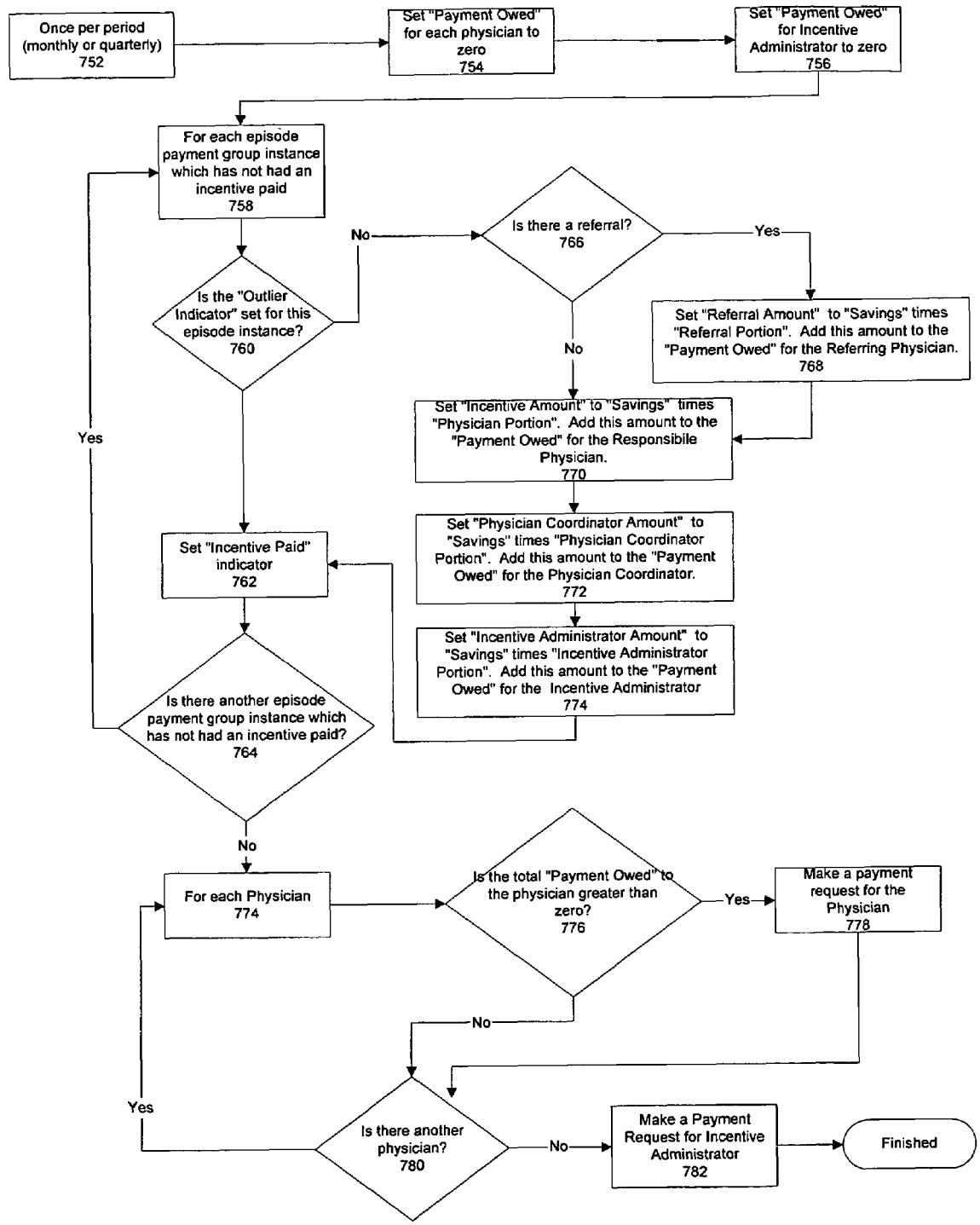
FIG. 13 illustrates a flowchart of providing incentive payments according to the present invention.

Once the step 700 calculate savings step is complete, then the step 750 payment of incentives takes place, as illustrated in FIG. 5 and shown in further detail in FIG. 13. On some preferably periodic basis, as shown in step 752, for each responsible physician, incentive payments based on the accumulated savings for that period are determined. Step 754 sets an incentive payment owed field associated with each responsible physician/provider 20 to zero, and similarly in step 756 the incentive payment owed to the incentive administrator 40 is set to zero. Thereafter, in step 758, each closed EPG instance is operated upon, and in step 760, a determination is made whether the outlier indicator has been set for that instance. If it has, that indicates that the particular instance being operated upon will not be used for purposes of incentives calculations and thus in step 762 an incentive indicator paid field is set to indicate that the incentive has been determined—to be zero, but nonetheless determined.

Step 764 follow and a determination is made whether there is another EPG instance corresponding to a closed episode that needs to be operated upon. If not, then the incentive payment calculations are finished, and if so, then another EPG instance is operated upon, as described above and hereinafter.

If, however, in step 760 the outlier indicator was not set, then for that instance step 766 follows and a determination is made whether the referral indicator, described above, that is associated with this instance, had been set. If not, then a referral portion of the savings must be attributed to the referring physician, and if not, then the savings for the instance can be divided between only the responsible provider 20, the payer 30, and the incentive administrator 40. With no referral, the preferred percentage is split equally in third, as discussed above, and with a referral, a small percentage is provided to the referring physician, with the remainder split in thirds.

Figure 12:
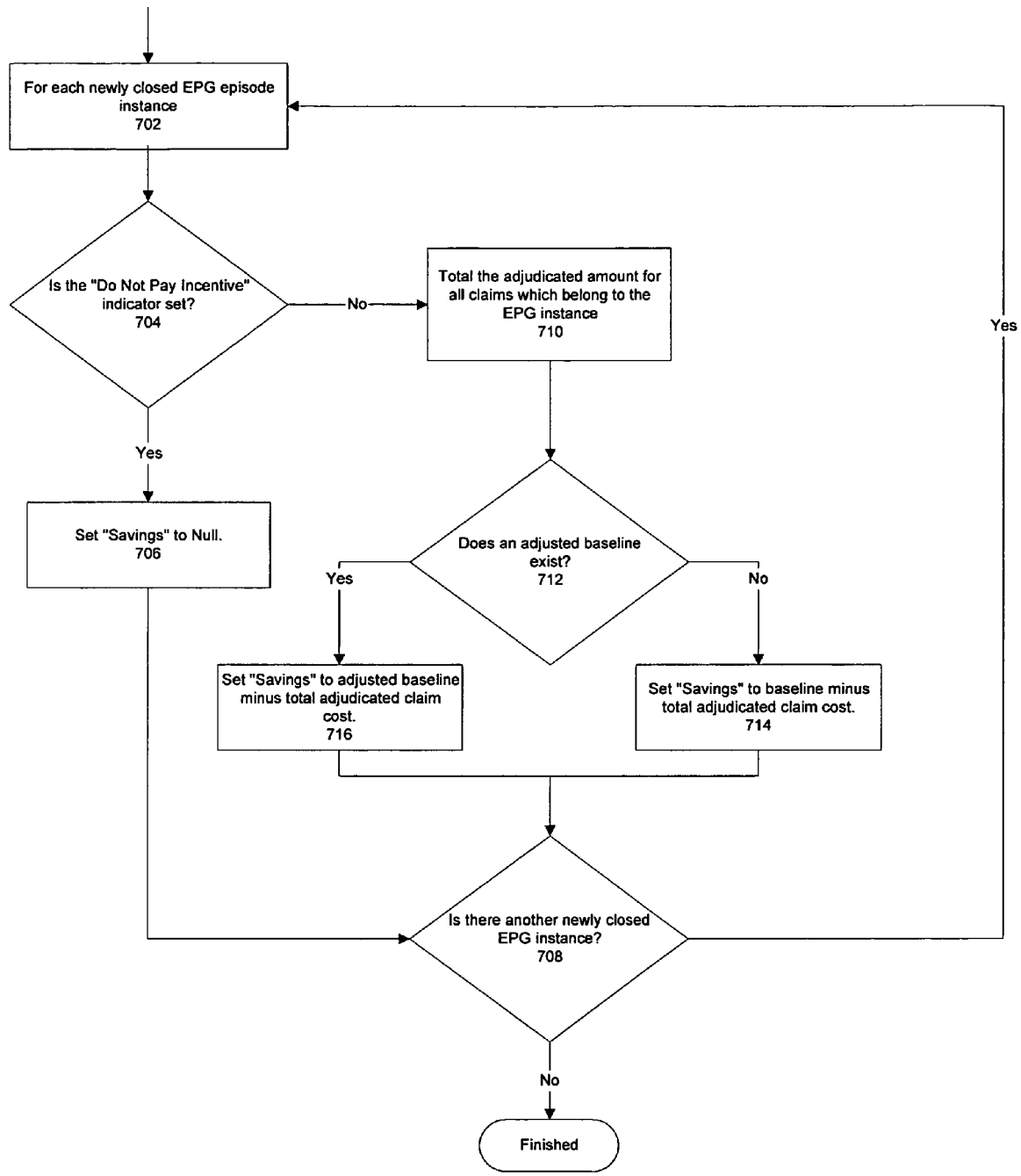
FIG. 12 illustrates a flowchart of determining savings for an closed episode of care according to the present invention.

If the referral indicator was set, then step 768 follows and a determination is made of the referral amount for the referring physician/provider based upon the referral amount factor that is being used multiplied by the savings previously determined from FIG. 12 for that instance. This amount is added to the payment owed for that referring physician/provider.

Thereafter follows step 770, which determined the amount owed to the responsible physician/provider 20. This will preferably follow step 766 if there was no referring physician, and will follow the step 768 determination if there was. In step 770, the physician/providers 20 incentive is determined by multiplying the savings previously determined from FIG. 12 with the responsible physician/provider factor. This incentive is preferably one-third of the total savings if there was no referral and without any portion being attributed to the physician coordinator, and will be somewhat less if there was a referral or an amount attributed to the physician coordinator. The amount determined as the incentive amount for this instance is then added to the payment owed field for the responsible physician/provider 20.

Thereafter, in step 772, that percentage, if any, that this attributable to the physician coordinator is determined and the incentive amount for this instance is then added to the payment owed field for that physician coordinator. Similarly, in step 774 which follows, for that instance, the incentive administrators 40 incentive is determined by multiplying the savings previously determined from FIG. 12 with the incentive administrator factor, which is preferably one-third the savings if there was no referral, and will be somewhat less if there was a referral, as described above. The amount determined as the incentive amount for this instance is then added to the payment owed field for the incentive administrator 40.

Thereafter, with the incentives determined for that instance, the incentive paid indicator is set in step 762 and each instance is operated upon as described above.

Step 774 follows, and for each physician it is then determined in step 776 whether that physician should receive an incentive award for that period. If so, then step 779 follows and a payment request is made for that physician. Step 780 queries whether payment requests for another physician are needed so that the previous steps 776 and 778 can be repeated for each. If not, then step 782 follows and a payment request for the incentive administrator 40 is also made.

Thus, the determined payment owed to each different responsible physician/provider 20 and the incentive administrator, related to the various completed episodes that took place during the period being operated upon, can be provided to the payer 20 so that payment can be made. It should be noted that determination of the payment owed to the responsible physician/providers 20 and the incentive administrator 40 implicitly determines the savings retained by the payer 30. It is apparent that other specific methods of calculating the incentive payments can be implemented and still be within the scope of the present invention.

While the present invention has been described herein with reference to particular embodiments thereof, a latitude of modification, various changes and substitutions are intended in the foregoing disclosure. For instance, the specific order that various determinations of incentives, indicators and the like are made, and the specific use of indicators are a design choice to the extent that there are other manners of deriving the same information. It is thus more significant that those considerations deemed important for the particular implementation of the incentive system according to the present invention are taken into account and used when implementing a specific system. It should thereby be appreciated that in some instances some features of the invention will be employed without a corresponding use of other features without departing from the spirit and scope of the invention as set forth in the appended claims.

The invention claimed is:

1. A computer-implemented method, executed in a first computer operated by an incentive administrator that is coupled to a second computer operated by a payer and a third computer operated by a healthcare provider, of providing an apportioned monetary incentive upon completion of a course of treatment for a patient with a condition during an episode of care, the method comprising the steps of:

identifying a responsible provider from among one or more healthcare providers involved in the course of treatment, based on performance of a defining procedure in the course of treatment;

creating an initial baseline value related to the course of treatment;

receiving over the computer network from the payers a diagnosis of the patient performed by a healthcare provider and provided to the payer, along with an associated cost quantified by the initial baseline value;

creating an episode of care based upon the diagnosis of the healthcare provider and the course of treatment for the condition;

verifying that the episode of care is not an outlier case representing an extreme condition that costs significantly more than the cost associated with the initial baseline value;

summing a plurality of claims processed during the episode of care to obtain a total treatment cost;

adjusting the initial baseline value by factoring in any effects due to comorbidity to derive an adjusted baseline value;

determining if the total treatment cost is less than the adjusted baseline value, thus resulting in a cost savings for the decided course of treatment;

representing the cost savings as an incentive payment that is to be apportioned among the responsible provider, the payer and the incentive administrator;

causing a first portion of the cost savings to be sent to the responsible provider in the form of a monetary incentive that is individually calculated based on the episode of care, and correlated to the total treatment cost;

causing a second portion of the cost savings to be sent to the payer, the second portion constituting a savings in the amount paid out for the course of treatment; and causing a third portion of the cost savings to be retained by the incentive administrator, wherein the responsible provider, the payer, and the incentive administrator are independent entities.

2. A computer-implemented method according to claim 1 wherein the initial baseline value represents a typical cost for providing treatment for the episode of care, the method further comprising the step of verifying that the episode of care is not subject to gaming effects.

3. A computer-implemented method according to claim 2 wherein the payer comprises an insurance company.

4. A computer-implemented method according to claim 3 where the step of creating the initial baseline value establishes the initial baseline value using a plurality of data relating to a plurality of previous episodes of care for the same condition.

5. A computer-implemented method according to claim 4 wherein prior to the step of creating the initial baseline is the step of filtering to remove outlier episodes of care for the same condition to thereby establish the plurality of data relating to a plurality of previous episodes of care for the same condition.

6. A computer-implemented method according to claim 1 further comprising the step of providing post analysis comparative data to the healthcare provider, the post analysis comparative data containing suggestions on how services can be provided in a more cost-effective manner.

7. A computer-implemented method according to claim 1 wherein during the treatment of the patient for the condition during the episode of care the patient encounters an additional condition that creates another episode of care and the step of adjusting the initial baseline value further includes the step of factoring in the additional condition, the method further including the steps of:

associating another baseline value related to the treatment of the additional condition, the another baseline value being adjusted to account for the condition;

summing another plurality of claims processed for the another episode of care of the patient for the additional condition to obtain another total treatment cost; and determining another monetary incentive to provide to the responsible provider if the another total treatment cost is less than the another baseline value.

8. A computer-implemented method according to claim 1 further comprising determining a factor for calculating a partial incentive payment in the event the patient does not complete the course of treatment.

9. The method of claim 1 wherein the defining procedure is selected from the group consisting of: the most significant procedure associated with the course of treatment; the incurring of a predetermined percentage of costs for the episode of care; and a termination procedure associated with the condition.

10. The method of claim 9 wherein the predetermined percentage of costs is within the range of 85% to 100% of total costs for the course of treatment.

11. The method of claim 1 further comprising the steps of:
comparing the cost incurred by the responsible provider against the adjusted baseline value; and
providing suggestions to the responsible provider in the event that the cost incurred exceeded the adjusted baseline value by a pre-determined amount.

12. The method of claim 11 further wherein the step of providing suggestions includes suggesting a change in utilization of healthcare resources by the responsible provider to reduce costs associated with the course of treatment in order to increase the first portion of cost savings available as a monetary incentive to the responsible provider.

13. The method of claim 12 further comprising the steps of:
comparing the cost incurred by the responsible provider against one or more baseline values for similar episodes of care, each performed by different responsible providers; and
providing suggestions to the responsible provider in the event that the cost incurred exceeded the at least one of the one or more baseline values by the pre-determined amount.

14. The method of claim 1 wherein the first portion, second portion, and third portion each comprise one-third of the cost savings.

15. An apparatus for determining an amount of an apportioned monetary incentive, as determined by an incentive administrator and payable to a physician responsible for a course of treatment of a patient with a condition during an episode of care comprising:

a first computer system operated by the incentive administrator, including:

means for identifying a responsible physician from among one or more physicians involved in the course of treatment, based on performance of a defining procedure in the course of treatment;

means for creating an initial baseline value related to the course of treatment;

means for receiving from a second computer system operated by a payer communicably coupled to the physician, data including the patient identity and a diagnosis of the patient, along with an associated cost quantified by the initial baseline value;

means for creating an episode of care based upon the diagnosis and the decided course of treatment;

means for summing a plurality of claims processed during the episode of care of the patient for the condition to obtain a total treatment of cost;

means for verifying that the episode of care is not an outlier case representing an extreme condition that costs significantly more than the cost associated with the initial baseline value;

means for adjusting the initial baseline value by factoring in cost offsets due to comorbidity effects;

means for determining if the total treatment cost is less than the adjusted baseline value, thus resulting in a cost savings for the decided course of treatment; and means for determining a first percentage of the cost savings to be paid to the responsible physician as a monetary incentive that is individually calculated based on the episode of care, and correlated to the total treatment cost;

means for determining a second percentage of the cost savings to be given to the payer, and representing a savings in the amount paid out for the course of treatment; and means for determining a third percentage of the cost savings to be retained by the incentive administrator, wherein the responsible physician, the payer, and the incentive administrator are independent entities.

* * * * *